(12) United States Patent
Lee et al.

(10) Patent No.: US 9,527,910 B2
(45) Date of Patent: Dec. 27, 2016

(54) ANG-2 SPECIFIC ANTIBODIES AND USES THEREOF

(71) Applicant: Samsung Electronics Co., Ltd., Suwon-si, Gyeonggi-do (KR)

(72) Inventors: Yoon Sook Lee, Hwaseong-si (KR); Chung Ho Kim, Yongin-si (KR); Kyung Eun Kim, Yongin-si (KR); Hyung-Chan Kim, Yongin-si (KR); Kwang Hoon Lee, Osan-si (KR); Hyo Seon Lee, Hwaseong-si (KR); Sang Yeul Han, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 87 days.

(21) Appl. No.: 14/322,343

(22) Filed: Jul. 2, 2014

(65) Prior Publication Data

US 2015/0010572 A1    Jan. 8, 2015

(30) Foreign Application Priority Data

Jul. 2, 2013 (KR) ........................ 10-2013-0077228

(51) Int. Cl.
*C07K 16/00* (2006.01)
*C07K 16/28* (2006.01)
*C07K 16/22* (2006.01)
*G01N 33/74* (2006.01)

(52) U.S. Cl.
CPC ............... *C07K 16/22* (2013.01); *G01N 33/74* (2013.01); *C07K 2317/34* (2013.01); *C07K 2317/76* (2013.01); *C07K 2317/92* (2013.01); *G01N 2333/515* (2013.01); *G01N 2800/7014* (2013.01)

(58) Field of Classification Search
None
See application file for complete search history.

(56) References Cited

U.S. PATENT DOCUMENTS

| | | | |
|---|---|---|---|
| 5,567,440 A * | 10/1996 | Hubbell | A61K 9/5031 424/484 |
| 5,859,205 A * | 1/1999 | Adair | C07K 16/18 530/387.1 |
| 7,973,140 B2 | 7/2011 | Green et al. | |
| 8,129,331 B2 | 3/2012 | Oliner et al. | |
| 8,268,314 B2 | 9/2012 | Baehner et al. | |
| 8,486,404 B2 | 7/2013 | Ryu et al. | |
| 8,703,130 B2 | 4/2014 | Baehner et al. | |
| 2006/0228363 A1* | 10/2006 | Arlen | C07K 16/303 424/155.1 |
| 2009/0226442 A1* | 9/2009 | Huet | C07K 16/2863 424/138.1 |
| 2009/0304694 A1 | 12/2009 | Oliner et al. | |
| 2011/0044998 A1* | 2/2011 | Bedian | A61K 39/39558 424/158.1 |
| 2011/0150895 A1 | 6/2011 | Ryu et al. | |
| 2011/0311546 A1 | 12/2011 | Oliner et al. | |
| 2012/0052073 A1 | 3/2012 | Green et al. | |
| 2012/0076796 A1 | 3/2012 | Gonzalez Pajuelo et al. | |
| 2012/0141499 A1 | 6/2012 | Oliner et al. | |
| 2012/0141500 A1 | 6/2012 | Brinkmann et al. | |
| 2012/0321627 A1 | 12/2012 | Baehner et al. | |
| 2013/0158234 A1 | 6/2013 | Oliner et al. | |
| 2013/0171160 A1 | 7/2013 | Green et al. | |
| 2015/0030603 A1* | 1/2015 | Kim | A61K 38/1891 424/139.1 |

FOREIGN PATENT DOCUMENTS

| | | |
|---|---|---|
| JP | 2010-189394 A | 9/2010 |
| KR | 2007-0116217 A | 12/2007 |
| KR | 2008-0100810 A | 11/2008 |
| KR | 2011-0055726 A | 5/2011 |
| KR | 2011-0068184 A | 6/2011 |

OTHER PUBLICATIONS

Klimka et al.,Human anti-CD30 recombinant antibodies by guided phage antibody selection using cell panning. British Journal of Cancer (2000) 83:252- 260.*
Paul, Fundamental Immunology, 3rd Edition, 1993, pp. 292-295.*
Eduardo Padlan, Anatomy of the antibody molecule. Mol Immunol. Feb. 1994;31(3):169-217.*
Beiboer et al., Guided selection of a pan carcinoma specific antibody reveals similar binding characteristics yet structural divergence between the original murine antibody and its human equivalent. J. Mol. Biol. 296: 833-849 (2000).*
Rudikoff et al Single amino acid substitution altering antigen-binding specificity. Proc Natl Acad Sci U S A. Mar. 1982;79(6):1979-83.*
Campbell A, General properties and applications of monoclonal antibodies, Elsevier Science Publishers, section 1.1, pp. 1-32, 1984.*
Owens RJ, Young RJ. The genetic engineering of monoclonal antibodies. J Immunol Methods. 168(2):149-165, 1994.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. 2002, Jul. 5, 320(2):415-28.*

(Continued)

*Primary Examiner* — Maher Haddad
(74) *Attorney, Agent, or Firm* — Leydig, Voit & Mayer, Ltd.

(57) ABSTRACT

Provided are an anti-Ang-2 antibody or antigen-binding fragment thereof that specifically binds to an angiogenesis-inducing factor Angiopoietin-2 (Ang-2), related compositions and pharmaceutical compositions, and methods for using such compositions and pharmaceutical compositions.

10 Claims, 5 Drawing Sheets

(56) References Cited

OTHER PUBLICATIONS

Felcht et al., Angiopoietin-2 differentially regulates angiogenesis through TIE2 and integrin signaling, *Journal of Clinical Investigation*, 122(6) 1991-2005 (2012).
Hanahan, Signaling Vascular Morphogenesis and Maintenance, *Science*, 277: 48-50 (1997).
Holopainen et al., Effects of Angiopoietin-2-Blocking Antibody on Endothelial Cell—Cell Junctions and Lung Metastasis, *Jour Natl Cancer Inst*, 104:461-475 (2012).
Hu et al., Angiopoietin 2 Induces Glioma Cell Invasion by Stimulating Matrix Metalloprotease 2 Expression through the $\alpha v \beta 1$ Integrin and Focal Adhesion Kinase Signaling Pathway, *Cancer Research*, 66(2): 775-783 (2006).
Imanishi et al., Angiopoietin-2 Stimulates Breast Cancer Metastasis through the $\alpha 5 \beta 1$ Integrin-Mediated Pathway, *Cancer Research*, 67(9): 4254-4263 (2007).
Maisonpierre et al., Angiopoietin-2, a Natural Antagonist for Tie2 That Disrupts in vivo Angiogenesis, *Science*, 277: 55-60 (1997).

\* cited by examiner

ANG-2 SPECIFIC ANTIBODIES AND USES THEREOF

CROSS-REFERENCE TO RELATED APPLICATIONS

This application claims the benefit of Korean Patent Application No. 10-2013-0077228 filed on Jul. 2, 2013 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 19,226 bytes ASCII (Text) file named "716760_ST25.TXT," created Jun. 30, 2014.

BACKGROUND

1. Field

The present disclosure relates to an anti-Ang-2 antibody specifically binding to an angiogenesis-inducing factor Angiopoietin-2 (Ang-2), and related compositions and methods utilizing such antibodies.

2. Description of the Related Art

Angiopoietin-2 (Ang-2) is an antagonistic ligand of a receptor Tie2 present at vascular endothelial cells and it suppresses signal transduction by Tie2 by competing with Angiopoietin-1 (Ang1), which is an agonist of Tie2, in binding Tie2. Ang1-Tie2 binding maintains the stability of vascular endothelial cells. Thus, interruption of this binding by Ang-2 may trigger signal transduction through this interruption, ultimately accelerating angiogenesis via the dynamic rearrangement of blood vessels.

As angiogenesis is an essential element for the growth of cancer, preventing the additional growth of cancer by inhibiting the function of Tie2-dependent Ang-2 to suppress angiogenesis has been known by the research of several preclinical models and in fact, various attempts to prevent the progress of cancer using antibodies specific to Ang-2 are ongoing.

Although there are phenomena showing that Ang-2 not only causes the growth of cancer through Tie2-dependent angiogenesis but also accelerates the metastasis of cancer through Tie2-independent mechanism, research results about the detailed mechanisms of action are yet to be elucidated.

As a method for effectively inhibiting the progress of cancer by Ang-2, it is believed to be important to suppress Tie2 signaling by Ang-2, and it is expected to be possible to secure cancer treatment agents with superior performance by blocking Tie2-independent mechanisms of Ang-2.

Accordingly, it is needed to elucidate Tie2-independent mechanisms of Ang-2 and to develop a substance suppressing them.

SUMMARY

Provided is an anti-Ang-2 antibody or antigen-binding fragment thereof that binds to angiogenesis-inducing factor Angiopoietin-2 (Ang-2), as well as a hybridoma cell line that produces the antibody.

Also provided are compositions, particularly pharmaceutical compositions, including an anti-Ang-2 antibody or an antigen-binding fragment thereof that binds to Angiopoietin-2 (Ang-2).

Also provided is a method of inhibiting angiogenesis, including administering the anti-Ang-2 antibody or an antigen-binding fragment thereof to a subject in need thereof.

A method of suppressing Ang-2-dependent cell adhesion is provided, including administering the anti-Ang-2 antibody or an antigen-binding fragment thereof to a subject in need thereof.

Further provided is a method of preventing and/or treating a disease related to angiogenesis and/or Ang-2-dependent cell adhesion, including administering the anti-Ang-2 antibody or an antigen-binding fragment thereof to a subject in need thereof.

Also provided is a method for detecting Ang-2, including treating a specimen obtained (isolated) from a subject with the anti-Ang-2 antibody or antigen-binding fragment thereof; and identifying the presence of an antigen-antibody reaction.

DETAILED DESCRIPTION

Figure 1:
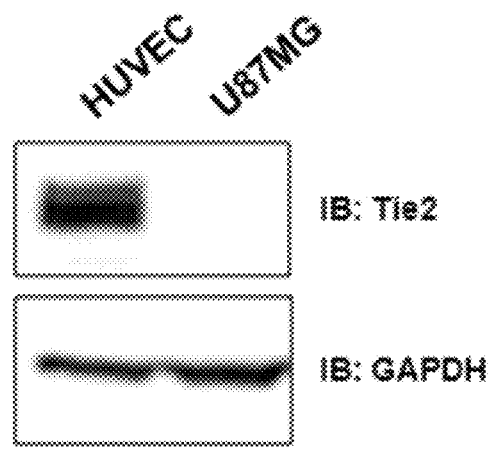
FIG. 1 is a picture of an electrophoresis gel demonstrating that Tie2 is not expressed in a U87MG cell line.

Ang-2 protein can not only cause the growth of cancer through Tie2-depedent angiogenesis, but also accelerate the metastasis of cancer through Tie2-independent mechanisms. For instance, in a cancer cell line where Ang-2 was manipulated to be overexpressed, the migration and invasion of cells, and cancer metastasis in a xenograft model were increased. In this connection, the inventors have confirmed Tie2-independent and Ang-2-dependent cell adhesion by measuring whether U87MG, a glioblastoma cancer cell line which does not express Tie2, can adhere to a surface coated with Ang-2.

The inventors also have found that Ang-2 is bound to a cell binding protein known as integrin and antibodies that inhibit binding between Ang-2 and integrin suppress Tie2-independent and Ang-2-dependent cell adhesion. According to one embodiment, the antibodies to be provided in the invention effectively suppress not only angiogenesis but also cancer metastasis.

One embodiment of the present disclosure provides an anti-Ang-2 antibody that specifically binds to an angiogenesis inducing factor Ang-2 (Angiopoietin-2), or an antigen-binding fragment thereof.

In another embodiment, the anti-Ang-2 antibody or the antigen-binding fragment thereof not only suppresses Ang-2 activity but also inhibits the binding between Ang-2 and integrin.

In connection with the angiogenesis process in a cancer tissue, vessel co-option occurs wherein cancer cells select pre-existing blood vessels to form new blood vessels in a cancer tissue. Thereafter, blood vessel regression occurs during which the functions of the pre-existing blood vessels are destroyed by the angiopoietin-2 pathway. The regression of the pre-existing vessels causes a hypoxic environment within the cancer tissue, which is an environment where the formation of new blood vessels is possible. Under such conditions, the expression of vascular endothelial cell growth factor (VEGF) is increased, and new blood vessels are thus formed. As angiopoietin proteins, Ang-1, Ang-2, Ang-3, and Ang-4 have been known and of them, Ang-2, is also known as ANGPT2 and is expressed in blood vessel remodeling areas.

An Ang-2 protein which serves as an antigen of the antibodies provided in the invention is closely related to angiogenesis, is a soluble ligand present in the blood, and has broad functions such as angiogenesis, metastasis, and cancer cell invasion.

The Ang-2 referred to herein may be derived from mammals including primates such as humans and monkeys and rodents such as mice and rats and for example, it may be human Ang-2 (e.g., NCBI Accession No. O15123, etc.), monkey Ang-2 (e.g., NCBI Accession No. Q8MIK6, etc.), mouse Ang-2 (e.g., NCBI Accession No. O35608, etc.), and rat Ang-2 (e.g., NCBI Accession No. O35462, etc.), but is not limited thereto.

An integrin is a common protein which mediates cell adhesion and has a heterodimer structure including an alpha (α) subunit and a beta (β) subunit. In mammals, 18 types of alpha subunits and 8 types of beta subunits have been identified. The integrin may be derived from mammals including primates such as humans and monkeys and rodents such as mice and rats and for example, it may be a human integrin, a monkey integrin, a mouse integrin and a rat integrin, but is not limited thereto. In each and every species, 24 types of integrins have been known and amino acid sequences thereof have been well identified so that they are clear matters to those who have ordinary knowledge in the art to which the invention pertains. For example, typical human integrin types may include alpha5beta1(α5β1) (α5: NCBI Accession No. P08648, β1: NCBI Accession No. P05556), alphaVbeta1(αVβ1) (αV: NCBI Accession No. P06756, β1: NCBI Accession No. P05556), and alphaVbeta3(αVβ3) (αV: NCBI Accession No. P06756, β3: NCBI Accession No. P05106).

The integrin of which the binding with Ang-2 is inhibited by the anti-Ang-2 antibody may be a human integrin and specifically, it may be selected from the group consisting of alpha5beta1(α5β1) (α5: NCBI Accession No. P08648, β1: NCBI Accession No. P05556), alphaVbeta1(αVβ1) (αV: NCBI Accession No. P06756, β1: NCBI Accession No. P05556), and alphaVbeta3(αVβ3) (αV: NCBI Accession No. P06756, β3: NCBI Accession No. P05106) and for example, it may be alpha5beta1(α5β1) (α5: NCBI Accession No. P08648, β1: NCBI Accession No. P05556), or alphaVbeta3(αVβ3) (αV: NCBI Accession No. P06756, β3: NCBI Accession No. P05106) but is not limited thereto.

The antibody has cell adhesion inhibitory effects and suppresses angiogenesis in cancer tissue by hindering the binding between Ang-2 and integrin along with its binding activity to Ang-2. Accordingly, the antibody has not only treatment effects for diseases related to angiogenesis but also cancer metastasis inhibitory effects.

The anti-Ang-2 antibody may be those recognizing as an epitope all or part (for example, of the loop, at least one amino acid residue selected from the group consisting of the amino acid residue exposed to the outside) of loop 1 (region from $417^{th}$ amino acid to $434^{th}$ amino acid of SEQ ID NO: 28) of human Ang-2 (hAng-2; SEQ ID NO: 28; Accession #O15123) or amino acid sequence regions including 2 to 20, 2 to 15, 2 to 10, or 2 to 5 contiguous amino acids on primary, secondary or tertiary structure including at least one amino acid residue exposed to the outside in loop 1 among SEQ ID NO: 28, or specifically binding thereto.

```
Ang-2
                                              (SEQ ID NO: 28)
MWQIVFFTLS  CDLVLAAAYN  NFRKSMDSIG  KKQYQVQHGS

CSYTFLLPEM  DNCRSSSSPY  VSNAVQRDAP  LEYDDSVQRL

QVLENIMENN  TQWLMKLENY  IQDNMKKEMV  EIQQNAVQNQ

TAVMIEIGTN  LLNQTAEQTR  KLTDVEAQVL  NQTTRLELQL

LEHSLSTNKL  EKQILDQTSE  INKLQDKNSF  LEKKVLAMED

KHIIQLQSIK  EEKDQLQVLV  SKQNSIIEEL  EKKIVTATVN

NSVLQKQQHD  LMETVNNLLT  MMSTSNSAKD  PTVAKEEQIS

FRDCAEVFKS  GHTTNGIYTL  TFPNSTEEIK  AYCDMEAGGG

GWTIIQRRED  GSVDFQRTWK  EYKVGFGNPS  GEYWLGNEFV

SQLTNQQRYV  LKIHLKDWEG  NEAYSLYEHF  YLSSEELNYR

IHLKGLTGTA  GKISSISQPG  NDFSTKDGDN  DKCICKCSQM

LTGGWWFDAC  GPSNLNGMYY  PQRQNTNKFN  GIKWYYWKGS

GYSLKATTMM  IRPADF
```

For example, the anti-Ang-2 antibody may be those recognizing as an epitope Q418 positioned at loop 1 of SEQ ID NO: 28 or amino acid sequence regions including 2 to 20, 2 to 15, 2 to 10, or 2 to 5 contiguous amino acids on primary, secondary or tertiary structure of the protein (Ang-2), including the amino acid residue of Q418 among SEQ ID NO: 28, or specifically binding thereto. The anti-Ang-2 antibody may be those further recognizing as an epitope P419 positioned at loop 1 of SEQ ID NO: 28 or amino acid sequence regions including 2 to 20, 2 to 15, 2 to 10, or 2 to 5 contiguous amino acids on primary, secondary or tertiary structure of the protein (Ang-2), including the amino acid residue of P419 among SEQ ID NO: 28, or specifically binding thereto, in addition to the above Q418 or amino acid sequence regions including the same. In one embodiment, the anti-Ang-2 antibody may be those recognizing the amino acid residues of Q418 and P419 as an epitope or specifically binding to them. The term "contiguous amino acids on primary, secondary or tertiary structure of Ang-2" may refer to the amino acids positioning contiguously on the primary, secondary or tertiary structure of the protein (i.e., Ang-2), and when the amino acids position contiguously on the tertiary structure of the protein, they may position contiguously or non-contiguously on the primary- or secondary-structure of the protein.

Q418, P419, or the amino acid regions including the same, the regions to which the anti-Ang-2 antibody specifically binds, are exposed amino acid residues positioned at loop 1 of the three dimensional structure of Ang-2, and they are considered to directly participate in binding between Ang-2 and integrin, or be included in the region that binds to integrin or positioned contiguously thereto (e.g., a "flanking" region). Hence, the anti-Ang-2 antibody or the antigen-binding fragment thereof competes with integrin to bind to Ang-2 and, accordingly, inhibits binding between Ang-2 and integrin.

Since not only the anti-Ang-2 antibody recognizing and/or specifically binding to the above regions but also an antibody or an antigen-binding fragment thereof competing with the Ang-2 antibody for binding to Ang-2 can compete with integrin to bind to Ang-2, the competing antibody or an antigen-binding fragment thereof can also inhibit binding between Ang-2 and integrin. Such competitively-binding antibodies may be antibodies recognizing the aforementioned regions and contiguous regions on the three dimensional structure as an epitope and/or a specific binding site. The competitively-binding antibodies may have binding affinity to Ang-2 of about 0.1 pM to about 50 nM, particularly about 0.5 pM to about 35 nM, and more particularly about 1 pM to about 10 nM.

Accordingly, the Ang-2 antibody or the antigen-binding fragment thereof of the invention may be one or more selected from the group consisting of an antibody or an antigen-binding fragment thereof recognizing the aforementioned regions as an epitope or specifically binding thereto, and an antibody or an antigen-binding fragment thereof which binds to Ang-2 in competition with the same.

In one embodiment, the above anti-Ang-2 antibody or the antigen-binding fragment thereof may include at least one (e.g., at least two, or three) complementarity determining region (CDR) of a heavy chain or a heavy chain variable region including the sane, wherein the CDR of a heavy chain may be at least one selected from the group consisting of:

a polypeptide (CDR-H1) including the amino acid sequence of SEQ ID NO: 1, a polypeptide (CDR-H2) including the amino acid sequence of formula 1 (SEQ ID NO: 14), and a polypeptide (CDR-H3) including an amino acid sequence selected from the group consisting of SEQ ID NO: 4 to SEQ ID NO: 6 (e.g., SEQ ID NOS: 4-6), wherein:

Formula 1 is

Y-I-X$_1$-Y-X$_2$-G-X$_3$-T-X$_4$-Y-N-P-S-L-K-S  (SEQ ID NO: 14)

wherein

X$_1$ is serine (S) or asparagine (N),

X$_2$ is serine (S) or arginine (R),

X$_3$ is serine (S) or asparagine (N), and

X$_4$ is serine (S) or aspartic acid (D).

In some embodiments, the antibody or antigen-binding fragment thereof includes a heavy chain with all three CDR regions (e.g., CDR-H1, CDR-H2, and CDR-H3) as described above.

The above anti-Ang-2 antibody or the antigen-binding fragment thereof may include at least one complementarity determining region (CDR) of a light chain or a light chain variable region including the sane, wherein the CDR of a light chain may be at least one selected from the group consisting of:

a polypeptide (CDR-L1) including the amino acid sequence of SEQ ID NO: 7 or SEQ ID NO: 8, a polypeptide (CDR-L2) including the amino acid sequence of SEQ ID NO: 9 or SEQ ID NO: 10, and a polypeptide (CDR-L3) including the amino acid sequence of formula 2 (SEQ ID NO: 15):

Formula 2

Q-Q-D-Y-X$_5$-S-P-X$_6$-T  (SEQ ID NO: 15)

wherein

X$_5$ is serine (S), or threonine (T), and

X$_6$ is proline (P), leucine (L), or tryptophan (W).

In some embodiments, the antibody or antigen-binding fragment thereof includes a light chain with all three CDR regions (e.g., CDR-L1, CDR-L2, and CDR-L3) as described above.

In another embodiment, the anti-Ang-2 antibody or the antigen-binding fragment thereof may include the heavy chain complementarity determining region(s), the light chain complementarity determining region(s), or a combination thereof.

More particularly, the anti-Ang-2 antibody or the antigen-binding fragment thereof may include at least one (or at least two or three) heavy chain complementarity determining region selected from the group consisting of a polypeptide (CDR-H1) including the amino acid sequence of SEQ ID NO: 1, a polypeptide (CDR-H2) including the amino acid sequence of SEQ ID NO: 2 or SEQ ID NO: 3, and a polypeptide (CDR-H3) including an amino acid sequence selected from the group consisting of SEQ ID NO: 4 to SEQ ID NO: 6, or a heavy chain variable region including the at least one heavy chain complementarity determining region;

at least one (or at least two or three) light chain complementarity determining region selected from the group consisting of a polypeptide (CDR-L1) including the amino acid sequence of SEQ ID NO: 7 or SEQ ID NO: 8, a polypeptide (CDR-L2) including the amino acid sequence of SEQ ID NO: 9 or SEQ ID NO: 10, and a polypeptide (CDR-L3) including an amino acid sequence selected from the group consisting of SEQ ID NO: 11 to SEQ ID NO: 13 or a light chain variable region including the at least one light chain complementarity determining region;

a combination of the at least one heavy chain complementarity determining region and the at least one light chain complementarity determining region; or a combination of the heavy chain variable region and the light chain variable region.

In particular, the heavy chain complementarity determining regions of the anti-Ang-2 antibody, for example, may have the amino acid sequences of the following Table 1.

TABLE 1

| Heavy Chain CDR Amino Acid Sequences | | |
|---|---|---|
| CDRH1-KABAT | CDRH2-KABAT | CDRH3-KABAT |
| DYAWN (SEQ ID NO: 1) | YISYSGSTSYNPSLKS (SEQ ID NO: 2) | STFGHYVSSMDY (SEQ ID NO: 4) |
| DYAWN (SEQ ID NO: 1) | YINYRGNTDYNPSLKS (SEQ ID NO: 3) | GNFEGAMDY (SEQ ID NO: 5) |

TABLE 1-continued

Heavy Chain CDR Amino Acid Sequences

| CDRH1-KABAT | CDRH2-KABAT | CDRH3-KABAT |
|---|---|---|
| DYAWN (SEQ ID NO: 1) | YISYSGSTSYNPSLKS (SEQ ID NO: 2) | GDYGNYVGPMDY (SEQ ID NO: 6) |

Likewise, the light chain complementarity determining regions of the anti-Ang-2 antibody, for example, may have the amino acid sequences of the following Table 2.

TABLE 2

Light Chain CDR Amino Acid Sequence

| CDRL1-KABAT | CDRL2-KABAT | CDRL3-KABAT |
|---|---|---|
| KASQSASNDVA (SEQ ID NO: 7) | YASNRYT (SEQ ID NO: 9) | QQDYSSPPT (SEQ ID NO: 11) |
| KASQSVSNDVA (SEQ ID NO: 8) | YASNRYP (SEQ ID NO: 10) | QQDYTSPWT (SEQ ID NO: 12) |
| KASQSVSNDVA (SEQ ID NO: 8) | YASNRYT (SEQ ID NO: 9) | QQDYSSPLT (SEQ ID NO: 13) |

In one embodiment, the anti-Ang-2 antibody or the antigen-binding fragment thereof may include
a heavy chain variable region including at least one heavy chain complementarity determining region selected from the group consisting of a polypeptide (CDR-H1) including the amino acid sequence of SEQ ID NO: 1, a polypeptide (CDR-H2) including the amino acid sequence of SEQ ID NO: 2 or SEQ ID NO: 3, and a polypeptide (CDR-H3) including an amino acid sequence selected from the group consisting of SEQ ID NO: 4 to SEQ ID NO: 6;
a light chain variable region including at least one light chain complementarity determining region selected from the group consisting of a polypeptide (CDR-L1) including the amino acid sequence of SEQ ID NO: 7 or SEQ ID NO: 8, a polypeptide (CDR-L2) including the amino acid sequence of SEQ ID NO: 9 or SEQ ID NO: 10, and a polypeptide (CDR-L3) including an amino acid sequence selected from the group consisting of SEQ ID NO: 11 to SEQ ID NO: 13; or
a combination of the heavy chain variable region and the light chain variable region.

The heavy chain variable region of the antibody according to one embodiment may include an amino acid sequence selected from the group consisting of SEQ ID NO: 16 to SEQ ID NO: 18:

```
                                        (SEQ ID NO: 16)
VQLQESGPGLVKPSQSLSLTCTVTGYSITSDYAWNWIRQFPGNKLEWMG
YISYSGSTSYNPSLKSRISITRDTSKNQFFLQLNSVTPEDTATYYCARS
TFGHYVSSMDYWGQ (SEQ ID NO: 17)
VQLQESGPGLVKPSQSLSLSCTVTGYSIASDYAWNWIRQFPGNKVEWMG
YINYRGNTDYNPSLKSRSSINRDTSKNQFFLQLNSVTTGDTATYYCARG
NFEGAMDYWGQ (SEQ ID NO: 18)
LQLQESGPGLVKPSQSLSLTCTVTGYSITSDYAWNWIRQFPGNKLEWMG
YISYSGSTSYNPSLKSRISITRDTSKNQFFLQLNSLTTEDTATYYCARG
DYGNYVGPMDYWGQ
(In the above SEQ ID NO: 16 to SEQ ID NO: 18, the
underlined bold letters are CDRH1, CDRH2, and
CDRH3 in order.)
```

The light chain of the antibody according to one embodiment may include an amino acid sequence selected from the group consisting of SEQ ID NO: 19 to SEQ ID NO: 21:

```
                                        (SEQ ID NO: 19)
SIVMTQTPKLLLVSAGDRVTITCKASQSASNDVAWYQQKPGQSPKLLIY
YASNRYTGVPDRFTGSGYGTDFTFAISTVQAEDLAIYFCQQDYSSPPTF
GGGTKLEIK (SEQ ID NO: 20)
TIVMTQTPKFLLVSAGDRITITCKASQSVSNDVAWYQQKPGQSPKLLIY
YASNRYPGVPDRFTGSGYGTDFTFTISTVQAEDLAVYFCQQDYTSPWTF
GGGTELEIK (SEQ ID NO: 21)
SIVMTQTPKFLLVSAGDRVTITCKASQSVSNDVAWYRQKPGQSPKLLIY
YASNRYTGVPDRFTGSGYGTDFTFTISTVQAEDLAVYFCQQDYSSPLTF
GARTKLELK
(In the above SEQ ID NO: 19 to SEQ ID NO: 21, the
underlined bold letters are CDRL1, CDRL2, and
CDRL3 in order.)
```

Accordingly, the anti-Ang-2 antibody or the antigen-binding fragment thereof may include a heavy chain variable region including an amino acid sequence selected from the group consisting of SEQ ID NO: 16 to SEQ ID NO: 18, a light chain variable region including an amino acid sequence selected from the group consisting of SEQ ID NO: 19 to SEQ ID NO: 21, or a combination of the heavy chain variable region and the light chain variable region.

For example, the anti-Ang-2 antibody or the antigen-binding fragment thereof may include
a heavy chain variable region including the amino acid sequence of SEQ ID NO: 16 and a light chain variable region including the amino acid sequence of SEQ ID NO: 19;
a heavy chain variable region including the amino acid sequence of SEQ ID NO: 17 and a light chain variable region including the amino acid sequence of SEQ ID NO: 20; or
a heavy chain variable region including the amino acid sequence of SEQ ID NO: 18 and a light chain variable region including the amino acid sequence of SEQ ID NO: 21.

In one embodiment, the anti-Ang-2 antibody or the antigen-binding fragment thereof may not be those including merely at least one amino acid sequence selected from the group consisting of SEQ ID NO: 8, SEQ ID NO: 10, and SEQ ID NO: 12, or may not be those including merely the amino acid sequence of SEQ ID NO: 20.

The anti-Ang-2 antibody or the antigen-binding fragment thereof may show the binding affinity (KD) in the range of not more than 10 nM, for example, about 1 pM to about 10 nM, or about 10 pM to about 10 nM, or about 100 pM to about 10 nM.

In another embodiment, there is provided a method for screening candidates for diagnosing, preventing, and/or treating a disease related to the activation and/or overproduction (overexpression) of angiopoietin-2 using the above epitope. The screening method may include
(a) contacting a candidate compound to the three dimensional structure epitope of the aforementioned angiopoietin-2; and
(b) measuring binding affinity between the epitope and the candidate compound. In the above screening method, in case that the epitope and the candidate compound show the binding affinity ($K_D$) in the range of not more than 10 nM, for example, about 1 pM to about 10 nM, or about 10 pM to about 10 nM, or about 100 pM to about 10 nM, the candidate compound can be determined to be a candidate for diagnosing, preventing, and/or treating a disease related to the activation and/or overproduction (overexpression) of angiopoietin-2.

The epitope may be all or part (for example, of the loop, at least one selected from the group consisting of the amino acid residues exposed to the outside) of loop 1 (region from $417^{th}$ amino acid to $434^{th}$ amino acid of SEQ ID NO: 28) of human Ang-2 (hAng-2; SEQ ID NO: 28; Accession #015123), or amino acid sequence regions including 2 to 20, 2 to 15, or 2 to 10 contiguous amino acids on primary, secondary or tertiary structure of Ang-2, including at least one amino acid residue exposed to the outside in loop 1 among SEQ ID NO: 28 and for example, it may be one or more selected from the group consisting of Q418 positioned at loop 1 of SEQ ID NO: 28, a combination of Q418 and P419, or an amino acid sequence region including 2 to 20, 2 to 15, 2 to 10, or 2 to 5 contiguous amino acids on primary, secondary or tertiary structure of Ang-2 including the same. The term "contiguous amino acids on primary, secondary or tertiary structure of Ang-2" may refer to the amino acids positioning contiguously on the on primary, secondary or tertiary structure of the protein (i.e., Ang-2), and when the amino acids position contiguously on the tertiary structure of the protein, they may position contiguously or non-contiguously on the primary- or secondary-structure of the protein.

The candidate compounds may be one or more selected from the group consisting of various artificially-synthesized or natural compounds, polypeptides, oligopeptides, polynucleotides, oligonucleotides, antisense-RNA, shRNA (short hairpin RNA), siRNA (small interference RNA), aptamers, natural product extracts and so on.

The step of measuring the binding affinity between the epitope and the candidate compound may be carried out using various methods known in the art. For example, the binding affinity may be measured using a Biacore machine. In general, the range within which the binding affinity is considered as a drug for treatment may be defined to have a binding constant KD value of not more than about 10 nM. For instance, in case that the binding affinity between the epitope of angiopoietin-2 and a candidate compound to be analyzed (for example, antibody) is about 0.1 pM to about 50 nM, particularly about 0.5 pM to about 35 nM, and more particularly about 1 pM to 10 nM when measured using surface plasmon resonance methods such as Biacore machine, the candidate compound (for example, antibody) can be determined to be a candidate for diagnosing, preventing, and/or treating a disease related to the activation and/or overproduction of angiopoietin-2.

In another embodiment, there is provided a polypeptide molecule including the heavy chain complementarity determining region, the light chain complementarity determining region or the combination thereof, or the heavy chain variable region, the light chain variable region or the combination thereof as described above. The polypeptide molecule may be included as a component of a protein scaffold (e.g., peptibody, nanobody, and the like), a bispecific antibody, and a multi-specific antibody having a similar structure and preparation to an antibody. The polypeptide molecule may include an amino acid sequence selected from the group consisting of SEQ ID NOs: 1 to 21.

In particular, the polypeptide molecule may include
one or more selected from the group consisting of a polypeptide including the amino acid sequence of SEQ ID NO: 1, a polypeptide including the amino acid sequence of formula 1 (SEQ ID NO: 14) (e.g., amino acid sequence of SEQ ID NO: 2 or SEQ ID NO: 3), and a polypeptide including an amino acid sequence selected from the group consisting of SEQ ID NO: 4 to SEQ ID NO: 6;
one or more selected from the group consisting of a polypeptide including the amino acid sequence of SEQ ID NO: 7 or SEQ ID NO: 8, a polypeptide including the amino acid sequence of SEQ ID NO: 9 or SEQ ID NO: 10, and a polypeptide including the amino acid sequence of formula 2 (SEQ ID NO: 15) (e.g., amino acid sequence selected from the group consisting of SEQ ID NO: 11 to SEQ ID NO: 13); or
a combination thereof.

In a specific embodiment, the polypeptide molecule may include an amino acid sequence selected from the group consisting of SEQ ID NOs: 16 to 18, an amino acid sequence selected from the group consisting of SEQ ID NO: 19 to SEQ ID NO: 21, or a combination thereof.

In one embodiment, the polypeptide molecule may not be those including merely at least one amino acid selected from the group consisting of SEQ ID NO: 8, SEQ ID NO: 10, and SEQ ID NO: 12, or may not be those including merely the amino acid sequence of SEQ ID NO: 20.

The above bispecific antibody or multi-specific antibody is referred to as an antibody including each antigen binding site to different two or more kinds of antigens and recognizing the two or more kinds of antigens at the same time, wherein one of the antigen binding sites may include the aforementioned polypeptide molecule. In particular, the polypeptide molecule serving as Ang-2 antigen binding site may form a dimer or multimer together with an antigen binding site to another antigen and then constitute a bi-specific antibody or a multi-specific antibody. Accordingly, in one embodiment, there is provided a bi-specific antibody or a multi-specific antibody including the polypeptide molecule as an Ang-2 antigen binding site.

In another embodiment, there is provided a protein scaffold including at least one (e.g., 1 to 5, particularly 2 to 4) peptide complex including one or more of the aforementioned polypeptide molecule or a repeat where the polypeptide molecules are repeatedly linked by a linker (hereafter, 'first peptide') and a polypeptide having a structural function (hereafter, 'second peptide'; e.g., heavy chain or light chain constant region of an antibody, or Fc fragment of an antibody) wherein the at least one peptide complex is bound to each other at the second peptide (e.g., Fc fragment) to form a multimer structure.

The antibody in the invention may include an animal-derived antibody, a chimeric antibody, a humanized antibody, or a fully human antibody. An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of an anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, have an important role in antigen binding into a human antibody framework.

It is important in CDR grafting technology for manufacturing a humanized antibody to select an optimized human antibody which can receive best the CDR of an animal-derived antibody and for this, utilization of antibody database, analysis of crystal structure, molecule modeling technology, etc. are employed. However, although the CDR of an animal-derived antibody is grafted into an optimized human antibody framework, there are a considerable number of cases where antigen binding affinity is not preserved because there are amino acids which affect antigen binding while being positioned at the framework of the animal-derived antibody. In this regard, it may be necessary to apply an additional antibody engineering technology for restoring antigen binding affinity.

According to one embodiment, the antibody may be a mouse-derived antibody, a mouse-human chimeric antibody, a humanized antibody, or a human antibody.

The term "antibody" as used in the invention refers to a substance produced by the stimulus of an antigen in immune system and its kinds are not particularly limited. Lately, the antibodies have been widely used for treating diseases. As the antibodies are very stable in vivo as well as in vitro and have a long half-life, they are favorable for mass expression and production. Also, since the antibody has intrinsically a dimer structure, it has a fairly high avidity.

An intact antibody has a structure with two full-length light chains and two full-length heavy chains, and each light chain is linked to each heavy chain via a disulfide bond. The constant region of an antibody is divided into a heavy chain constant region and a light chain constant region, and the heavy chain constant region has gamma (γ), mu (μ), alpha (α), delta (δ) and epsilon (ε) types, and has gamma1 (γ1), gamma2 (γ2), gamma3 (γ3), gamma4 (γ4), alpha1 (α1) and alpha2 (α2) as its subclass. The light chain constant region has kappa (κ) and lambda (λ) types.

The term "heavy chain" is understood to include a full-length heavy chain and fragments thereof, the full-length heavy chain including a variable region domain $V_H$ including an amino acid sequence having sufficient variable region sequences that contribute the specificity for antigen binding and three constant region domains $C_{H1}$, $C_{H2}$ and $C_{H3}$ domains and a hinge. The term "light chain" is understood to include a full-length light chain and fragments thereof, the full-length light chain including a variable region domain $V_L$ including an amino acid sequence having sufficient variable region sequences that contribute to the specificity for antigen binding and a constant region domain $C_L$.

The term "CDR (complementarity determining region)" refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope. Throughout the specification, the terms "specifically binding" or "specifically recognizing" has the same meaning as generally known to an ordinary person in the art, indicating that an antigen and an antibody specifically interact with each other to lead to an immunological response.

The antigen-binding fragment of an antibody provided in the invention may be a fragment including one or more of the complementarity determining region.

The term "antigen-binding fragment," which is a fragment of the full structure of an immunoglobulin, refers to some of a polypeptide including a portion to which an antigen can bind. For example, it may be a scFv, a (scFv)$_2$, a Fab, a Fab' or a F(ab')$_2$, but is not limited thereto.

Among the above antigen-binding fragments, a Fab, which is a structure having the light chain and heavy chain variable regions, the light chain constant region, and the heavy chain first constant region ($C_{H1}$), has one antigen binding site. A Fab' differs from the Fab in that the Fab' has a hinge region including at least one cysteine residue at the C-terminal of the heavy chain $C_{H1}$ domain. A F(ab')$_2$ is produced when cysteine residues at the hinge region of Fab' are joined by a disulfide bond. A Fv is a minimal antibody fragment, having only heavy chain variable regions and light chain variable regions, and a recombinant technique for producing the Fv fragment is well known in the art. A two-chain Fv may have a structure in which heavy chain variable regions are linked to light chain variable regions by a non-covalent bond, and a single-chain Fv may generally form a dimer structure as in the two-chain Fv, wherein heavy chain variable regions are covalently bound to light chain variable regions via a peptide linker or the heavy and light chain variable regions are directly linked to each other at the C-terminals thereof. The linker may be a peptide linker including 1 to 100 or 2 to 50 any amino acids, and proper sequences thereof have been known in the art. The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region included in the heavy chains of an antibody, which is present between the CH1 and CH2 regions, and provides flexibility to the antigen binding site in the antibody. For example, the hinge may be derived from a human antibody and particularly, it may be derived from IgA, IgE, or IgG, for example, IgG1, IgG2, IgG 3, or IgG4.

When an animal-derived antibody goes through a chimerization process, an animal-derived IgG1 hinge is replaced with a human IgG1 hinge, but a length of the animal-derived IgG1 hinge is shorter than the human IgG1 hinge, and disulfide bonds between two heavy chains are reduced from 3 to 2. Thus, rigidity of the hinges may have different effects. Therefore, modification of a hinge region can increase an antigen binding efficiency of a humanized antibody. Methods of deleting, inserting, or substituting an amino acid for modifying amino acid sequences of the hinge region are well known in the art.

Portions except the variable regions of the anti-Ang-2 antibody may be constant regions derived from a human antibody and particularly, they may be constant regions derived from IgA, IgD, IgE, or IgG, for example, IgG1, IgG2, IgG 3, or IgG4.

The anti-Ang-2 antibody may be a monoclonal antibody. The monoclonal antibody may be prepared by methods well known in the art. For example, it may be prepared using a phage display technique. Alternately, the Ang-2 antibody may be prepared into a mouse-derived monoclonal antibody by methods set forth in the paper written by Schwaber, et., al (Schwaber, J and Cohen, E. P., "Human×Mouse Somatic Cell Hybrid Clones Secreting Immunoglobulins of Both Parental Types," Nature, 244 (1973), 444-447).

Meanwhile, individual monoclonal antibodies may be screened using a typical ELISA (Enzyme-Linked ImmunoSorbent Assay) format, based on the binding potential with Ang-2. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang-2 may be each verified.

The remainder portions except the antigen binding portions of the finally selected antibodies may be prepared as not only human immunoglobulin antibodies but also humanized antibodies. Preparation of humanized antibodies is well known in the art (Almagro, J. C. and Fransson, J., "Humanization of antibodies," Frontiers in Bioscience, 13(2008), 1619-1633).

Another embodiment provides a hybridoma cell line which produces a monoclonal antibody of the anti-Ang-2 antibody. The hybridoma cell line may be KCLRF-BP-00292, KCLRF-BP-00293, or KCLRF-BP-00294 cell lines.

Another embodiment provides a pharmaceutical composition including the anti-Ang-2 antibody or an antigen-binding fragment thereof as an active ingredient.

Another embodiment provides a pharmaceutical composition for inhibiting angiogenesis, including the anti-Ang-2 antibody or an antigen-binding fragment thereof as an active ingredient.

Another embodiment provides a method of inhibiting angiogenesis, including administering a pharmaceutically effective amount of the anti-Ang-2 antibody or an antigen-binding fragment thereof to a subject in need of inhibiting angiogenesis. The method may further include the step of identifying the subject in need of inhibiting angiogenesis.

Another embodiment provides a pharmaceutical composition for suppressing cell adhesion, including the anti-Ang-2 antibody or an antigen-binding fragment thereof as an active ingredient.

Another embodiment provides a method of suppressing cell adhesion, including administering a pharmaceutically effective amount of the anti-Ang-2 antibody or an antigen-binding fragment thereof to a subject in need of suppressing cell adhesion. The method may further include the step of identifying the subject in need of suppressing cell adhesion.

Another embodiment provides a pharmaceutical composition for preventing and/or treating a disease related to angiogenesis and/or cell adhesion, including the anti-Ang-2 antibody or an antigen-binding fragment thereof as an active ingredient.

Another embodiment provides a method of preventing and/or treating a disease related to angiogenesis and/or cell adhesion, including administering a pharmaceutically effective amount of the anti-Ang-2 antibody or an antigen-binding fragment thereof to a subject in need of preventing and/or treating a disease related to angiogenesis and/or cell adhesion. The method may further include the step of identifying the subject in need of preventing and/or treating a disease related to angiogenesis and/or cell adhesion.

Another embodiment provides a composition for diagnosing a disease related to angiogenesis and/or cell adhesion, including the anti-Ang-2 antibody or an antigen-binding fragment thereof.

The cell adhesion is a major mechanism of cancer metastasis and particularly, it may be cell adhesion to cancer cells and it may be Ang-2-depedent cell adhesion.

The pharmaceutical composition may further include a pharmaceutically acceptable carrier, and the carrier may be those commonly used in the formulation of drugs, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include one or more selected from the group consisting of a diluent, an excipient, a lubricant, a wetting agent, a sweetener, a flavor enhancer, an emulsifying agent, a suspension agent, and a preservative.

An effective amount of the pharmaceutical composition, or the antibody, or the antigen-binding fragment thereof may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The content of the anti-Ang-2 antibody or the antigen-binding fragment thereof in the pharmaceutical composition may be prescribed in a variety of ways, depending on factors such as formulation methods, administration methods, age of patients, body weight, gender, pathologic conditions, diets, administration time, administration interval, administration route, excretion speed, and reaction sensitivity. For example, a daily dosage of the anti-Ang-2 antibody or the antigen-binding fragment thereof may be within the range of 0.001 to 1000 mg/kg, particularly 0.01 to 100 mg/kg, and more particularly 0.1 to 50 mg/kg, but is not limited thereto. The daily dosage may be formulated into a single formulation in a unit dosage form or formulated in suitably divided dosage forms, or it may be manufactured to be contained in a multiple dosage container.

The pharmaceutical composition may be formulated into a form of a solution in oil or an aqueous medium, a suspension, syrup, an emulsifying solution, an extract, powder, granules, a tablet, or a capsule, and may further include a dispersing or a stabilizing agent for the formulation.

In particular, the pharmaceutical composition including the anti-Ang-2 antibody or the antigen-binding fragment thereof may be formulated into an immunoliposome since it contains an antibody. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

Meanwhile, as the anti-Ang-2 antibody or the antigen-binding fragment thereof specifically binds to Ang-2, this can be used to detect Ang-2, and the presence of the overexpression of Ang-2 can be verified using this. Accordingly, another embodiment of the invention provides a composition for detecting Ang-2 and a composition for diagnosing a disease related to the overexpression of Ang-2, including the anti-Ang-2 antibody or the antigen-binding fragment thereof.

In another embodiment, there is provided a method for detecting Ang-2, including treating a specimen obtained (isolated) from a subject with the anti-Ang-2 antibody or the antigen-binding fragment thereof; and measuring the presence or the level of an antigen-antibody reaction. Also, there is provided a diagnosis method including treating a specimen obtained from a subject with the anti-Ang-2 antibody or the antigen-binding fragment thereof; and detecting the presence of an antigen-antibody reaction. The diagnosis method may further include determining the subject to have Ang-2 overexpression symptoms or to have a disease related to Ang-2 overexpression when the antigen-antibody reaction is detected. The specimen may be selected from the group consisting of cells, tissues, and body fluids (blood, serum, urine, saliva, and the like) obtained (isolated) from a subject.

The step of measuring the presence or the level of the antigen-antibody reaction may be performed using various methods known in the art. For example, it may be measured through an ordinary enzyme reaction, fluorescence, luminescence, and/or radioactivity detection and particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The subject which the pharmaceutical composition, or the anti-Ang-2 antibody or an antigen-binding fragment thereof is administered to or is aimed to diagnose may be mammals including primates such as humans and monkeys, or rodents such as rats and mice, or cells or tissues obtained (separated) therefrom.

The diseases related to the angiogenesis and/or cancer cell adhesion and/or Ang-2 overexpression may be cancer, cancer metastasis, retinopathy of prematurity, macular degeneration (e.g., age-related macular degeneration), diabetic retinopathy, eye diseases such as neovascular glaucoma, psoriasis, asthma, rheumatoid arthritis, pneumonia, inflammation diseases such as chronic inflammation, infection diseases, high blood pressure, arteriosclerosis, kidney-related diseases, septicemia, etc. The cancer may be those overexpressing Ang-2, it may be a solid cancer or a blood cancer, and it may be, but not limited to, selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastrointestinal cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, etc.

Previously, there were attempts to inhibit angiogenesis by inhibiting binding between Ang-2 and its receptor Tie2, but any inhibitors against binding between Ang-2 and integrin which is reported to play an important role in not only the migration, invasion, and metastasis of cancer cells but also the migration and invasion of vascular endothelial cells have not been known so far. Under such circumstance, the present disclosure proposes a novel method capable of inhibiting cancer cell metastasis by Ang-2 and angiogenesis, by suggesting an antibody capable of effectively blocking Ang-2-depedent cell adhesion and binding between Ang-2 and integrin. Also, the antibody suggested in the invention is expected to be applied to diagnose and treat a disease related to abnormal blood vessel formation. The antibody can be applied for combination therapy with chemical medicines and other anticancer drugs, and is expected to be employed for antibody fragments, bi- or multi-specific antibodies, protein scaffolds, etc. using Ang-2 specific recognition activity.

EXAMPLES

Hereafter, the present disclosure will be described in detail by examples.

The following examples are intended merely to illustrate the invention and are not construed to restrict the invention.

Example 1

Preparation of Anti-Ang-2 Antibody

A human Ang-2 protein (R&D systems; 623-AN-025/CF) was administered to 5-week-old BALB/c mice along with an adjuvant to induce an immune response and then, hybridomas that produce an individual anti-Ang-2 antibody were prepared according to the known methods described in the paper written by Schwaber, et., al (Schwaber, J and Cohen, E. P., "Human×Mouse Somatic Cell Hybrid Clones Secreting Immunoglobulins of Both Parental Types," Nature, 244 (1973), 444-447).

More specifically, to obtain immunized mice necessary for developing hybridoma cell lines, 100 µg of human Ang-2 protein (R&D Systems) mixed with the same amount of a complete Freund's adjuvant was administered via an intraperitoneal injection to each of five 5-week-old BALB/c mice (Japan SLC, Inc.). After two weeks, the antigen (half the previously injected amount) mixed with an incomplete Freund's adjuvant using the same method as described above was administered to each mouse via an intraperitoneal injection. After one additional week, a final boosting was performed and three days later, blood was collected from the tail of each mouse to obtain serum, which was then diluted at $\frac{1}{1000}$ with PBS and subjected to an ELISA to verify that the titer of an antibody recognizing Ang-2 was increased. From the results, mice in which a sufficient amount of the antibody was obtained were selected, and a cell fusion process was performed on the selected mice.

Three days before the cell fusion experiment, a mixture of 50 µg of PBS and 100 µg of human Ang-2 protein (R&D systems) was administered via an intraperitoneal injection to BALB/c mice (Japan SLC, Inc.), and after each immunized mouse was anesthetized, its spleen located on the left side of the body was extracted. The extracted spleen was ground with a mesh to isolate cells, which were mixed with a culture medium (DMEM, Hyclon) to prepare a spleen cell suspension. The suspension was centrifuged to collect a cell layer. The obtained $1 \times 10^8$ spleen cells were mixed with $1 \times 10^7$ myeloma cells (Sp2/0), and the mixture was centrifuged to precipitate the cells. The centrifuged precipitate was slowly dispersed, treated with 1 ml of 45% polyethylene glycol (PEG 1500) contained in a culture medium (DMEM), and maintained at 37° C. for one minute before adding 1 ml of a culture medium (DMEM). Subsequently, 10 ml of the culture medium (DMEM) was added for 1 minute to the resultant, which was incubated in a water bath at 37° C. for 5 minutes and then re-centrifuged after the total volume was made to reach 50 ml. The resulting cell precipitate was re-suspended in an isolation medium (HAT medium) at a concentration of $1 \sim 2 \times 10^5$/ml, and the resultant suspension was distributed at 0.1 ml to a 96-well plate, which was then incubated in a carbon dioxide incubator at 37° C. to prepare the hybridoma cell groups. The thus prepared hybridomas were deposited in the Korean Cell Line Bank located at Yongon-dong, Chongno-gu, Seoul, South Korea, as of Apr. 23, 2013 and received accession numbers KCLRF-BP-00292(7F8), KCLRF-BP-00293(8B3), and KCLRF-BP-00294(2E7), respectively.

Example 2

Manufacture of Anti-Ang-2 Antibody 2.1. Selection of Anti-Ang-2 Antibody Producing Clone and Purification of Antibody The above obtained individual antibody producing hybridomas were screened using a typical ELISA format to select hybridomas producing 95 anti-Ang-2 monoclonal antibodies among the hybridomas differentiated from their mother hybridomas, based on their binding potential with Ang-2.

More specifically, to select the hybridoma cells that specifically react only to Ang-2 protein among the hybridoma cell groups prepared in Example 1 above, an ELISA assay method using a human Ang-2 protein as an antigen was used for screening.

Human Ang-2 protein was added at 100 ng per well to a microtiter plate to attach to the surface of the plate, and unreacted antigens were removed by washing. 50 μl of the hybridoma cell culture obtained in Example 1 above was added to each well to react for 1 hour and then, the wells were sufficiently washed with phosphate buffered saline-TWEEN 20 (PBST) solution to remove unreacted culture solution. Goat anti-mouse IgG-horseradish peroxidase (goat anti-mouse IgG-HRP) was added thereto, a reaction was allowed to occur at a room temperature for 1 hour and then, washing was sufficiently performed with the PBST solution. Subsequently, substrate solution (OPD) of peroxidase was added to each well to react, and the reaction degree was evaluated by measuring the absorption at 450 nm using an ELISA reader to repeatedly select hybridoma cell lines that secret antibodies having specifically high binding affinity only to human Ang-2 protein. A limiting dilution was performed on the hybridoma cell lines obtained through repetitive selection to obtain final 58 clones of hybridoma cell lines producing monoclonal antibodies.

Each hybridoma obtained above was cultured in DMEM (Dulbeco's Modified Eagle's Medium) and then, the culture solutions were collected and subject to Protein G-affinity chromatography method to purify anti-Ang-2 monoclonal antibodies produced from each hybridoma.

First, the hybridoma cells cultured in 50 ml of culture medium (DMEM) containing 10% (v/v) FBS were centrifuged to obtain a cell precipitate, which was washed at least twice with 20 ml of PBS to remove the FBS. The cell precipitate was re-suspended in 50 ml of the culture medium (DMEM) and then incubated in a carbon dioxide incubator at 37° C. for 3 days. Subsequently, the cell culture was centrifuged to remove the antibody-producing cells, and the culture medium including the secreted antibodies was isolated and then, stored at 4° C. or used directly. Antibodies were purified from 50 to 300 ml of the culture medium using an AKTA purification device (GE Healthcare) equipped with an affinity column (protein G agarose column; Pharmacia, USA). The purified antibodies were stored for subsequent use after replacing the supernatant with PBS using a filter for protein aggregation (Amicon). The antibodies obtained from each hybridoma above were named 7F8 (KCLRF-BP-00292), 8B3 (KCLRF-BP-00293), and 2E7 (KCLRF-BP-00294), respectively.

The binding affinities of the above 3 kinds of antibodies to human Ang-2 protein were measured by a SPR technology using a BIAcore T100 (GE Healthcare). The SPR technology uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CM5 sensor chip (GE healthcare) up to 8,000 RU levels using a pH 5.0 acetate solution and an amine coupling kit (GE Healthcare). A recombinant hAng-2 (C-His, R&D Systems) protein was flowed onto the chip to be captured at 100 to 200 RU levels. The antibodies obtained in Example 2 above were diluted serially to twice each time starting from 100 nM concentration and each of them was flowed onto the chip to allow them to be bound to (on), dissociated from (off), and regenerated (using 10 mM NaOH solution) from the antigen captured on the sensor chip, thereby to measure antigen-antibody affinities. With regard to hAng2, such experiments were conducted, and the results are as shown in the following Table 3.

TABLE 3

| Antibody Name | hAng-2 (Kd) |
| --- | --- |
| SAIT-Ang-2-AB-m7F8 | 4.2 pM |
| SAIT-Ang-2-AB-m8B3 | 8.6 pM |
| SAIT-Ang-2-AB-m2E7 | 30.6 nM |

2.2. Gene Cloning of Anti-Ang-2 Antibody

A whole RNA was obtained using RNeasy mini kit (Qiagen) from each antibody-producing hybridoma ($2 \times 10^6$ cells) obtained from Example 2.1 above. Then, by using this as a template, only the gene sequence of the heavy chain and light chain variable regions of the monoclonal antibody to be produced in each hybridoma was amplified using a OneStep RT-PCR kit (Qiagen), a Mouse Ig-Primer Set (Novagen), and a therrmocycler (GeneAmp PCR System 9700, Applied Biosystem) under the following conditions: 5 min at 94° C.; [30 min. at 50° C., 15 min. at 95° C.], [1 min. at 94° C., 1 min. at 50° C., 2 min. at 72° C.]×35 cycles; 6 min. at 72° C.; cooling to 4° C.

The PCR products obtained from each reaction were subject to a direct DNA sequencing to obtain the CDR, heavy chain variable regions and light chain variable regions of each antibody, and DNA sequences encoding them, and the obtained results are set forth in the following Tables 4 to 7.

TABLE 4

| | Heavy Chain CDR Sequence | | |
| --- | --- | --- | --- |
| Antibody Name | CDRH1-KABAT | CDRH2-KABAT | CDRH3-KABAT |
| SAIT-Ang-2-AB-m7F8 | DYAWN (SEQ ID NO: 1) | YISYSGSTSYNPSLKS (SEQ ID NO: 2) | STFGHYVSSMDY (SEQ ID NO: 4) |
| SAIT-Ang-2-AB-m8B3 | DYAWN (SEQ ID NO: 1) | YINYRGNTDYNPSLKS (SEQ ID NO: 3) | GNFEGAMDY (SEQ ID NO: 5) |
| SAIT-Ang-2-AB-m2E7 | DYAWN (SEQ ID NO: 1) | YISYSGSTSYNPSLKS (SEQ ID NO: 2) | GDYGNYVGPMDY (SEQ ID NO: 6) |

TABLE 5

Light Chain CDR Amino Acid Sequence

| Antibody Name | CDRL1-KABAT | CDRL2-KABAT | CDRL3-KABAT |
|---|---|---|---|
| SAIT-Ang-2-AB-m7F8 | KASQSASNDVA (SEQ ID NO: 7) | YASNRYT (SEQ ID NO: 9) | QQDYSSPPT (SEQ ID NO: 11) |
| SAIT-Ang-2-AB-m8B3 | KASQSVSNDVA (SEQ ID NO: 8) | YASNRYP (SEQ ID NO: 10) | QQDYTSPWT (SEQ ID NO: 12) |
| SAIT-Ang-2-AB-m2E7 | KASQSVSNDVA (SEQ ID NO: 8) | YASNRYT (SEQ ID NO: 9) | QQDYSSPLT (SEQ ID NO: 13) |

TABLE 6

| Antibody Name | Heavy Chain Variable Region Sequence |
|---|---|
| SAIT-Ang-2-AB-m7F8 | VQLQESGPGLVKPSQSLSLTCTVTGYSITSDYAWNWIRQFPGNKLEWMGYISYSGSTSYNPSLKSRISITRDTSKNQFFLQLNSVTPEDTATYYCARSTFGHYVSSMDYWGQ (SEQ ID NO: 16)<br><br>gatgtgcagcttcaggagtcgggacctggcctggtgaaaccttctcagtctctgtccctcacctgcactgtcactggctactcaatcaccagtgattatgcctggaactggatccggcagtttccaggaaacaaactggagtggatgggttacataagctacagtggtagcactagctacaacccatctctcaaaagtcgaatctctatcactcgagacacatccaagaatcagttcttcctgcagctgaattctgtgacacctgaggacacagccacatattactgtgcaagatcaacttttggtcactacgtcagttctatggactactggGGTCAAGGAACCTCAGTCACCGTCTCCTCA (SEQ ID NO: 22) |
| SAIT-Ang-2-AB-m8B3 | VQLQESGPGLVKPSQSLSLCTVTGYSIASDYAWNWIRQFPGNKVEWMGYINYRGNTDYNPSLKSRSSINRDTSKNQFFLQLNSVTTGDTATYYCARGNFEGAMDYWGQ (SEQ ID NO: 17)<br><br>gatgtgcagcttcaggagtcgggacctggcctggtgaaaccttctcagtctctgtccctcctgcactgtcactggctactcaatcgccagtgattatgcctggaactggatccggcagtttccaggaaacaaagtggagtggatgggctacataaactaccgtggaaacactgactacaacccatctctcaaaagtcgaagctctatcaatcgagacacatccaagaaccagttcttcctgcaattgaattctgtgactactggggacacagccacatattactgtgcaagaggtaacttcgaaggagctatggactactggGGTCAAGGAACCTCAGTCACCGTCTCCTCA (SEQ ID NO: 23) |
| SAIT-Ang-2-AB-m2E7 | LQLQESGPGLVKPSQSLSLTCTVTGYSITSDYAWNWIRQFPGNKLEWMGYISYSGSTSYNPSLKSRISITRDTSKNQFFLQLNSLTTEDTATYYCARGDYGNYVGPMDYWGQ (SEQ ID NO: 18)<br><br>gatgtgcagcttcaggagtcgggacctggcctggtgaaaccttctcagtctctgtccctcacctgcactgtcactggctactcaatcaccagtgattatgcctggaactggatccggcagtttccaggaaacaaactggagtggatgggctacataagctacagtggtagtactagctacaacccatctctcaaaagtcgaatctctatcactcgagacacatccaagaaccagttcttcctacagttgaattctttgactactgaggacacagccacatattactgtgcaagaggggactatggtaactacgtgggacctatggactactggGGTCAAGGAACCTCAGTCACCGTCTCCTCA (SEQ ID NO: 24) |

TABLE 7

| Antibody Name | Light Chain Variable Region Sequence |
|---|---|
| SAIT-Ang-2-AB-m7F8 | SIVMTQTPKLLLVSAGDRVTITCKASQSASNDVAWYQQKPGQSPKLLIYYASNRYTGVPDRFTGSGYGTDFTFAISTVQAEDLAIYFCQQDYSSPPTFGGGTKLEIK (SEQ ID NO: 19)<br><br>agtattgtgatgacccagactcccaaactcctgcttgtttcagcaggagacagggttaccataacctgcaaggccagtcagagtgcgagcaatgatgttgcttggtaccaacagaagccagggcagtctcctaaactgctgatatactatgcatccaatcgctacactggagtccctgatcgcttcactggcagtggatatgggacggatttcactttcgccatcagcactgtgcaggctgaagacctggcaatttatttctgtcagcaggattatagctctccaccgacgttcggtggaggcaccaagctggaaatcaaa (SEQ ID NO: 25) |
| SAIT-Ang-2-AB-m8B3 | TIVMTQTPKFLLVSAGDRITITCKASQSVSNDVAWYQQKPGQSPKLLIYYASNRYPGVPDRFTGSGYGTDFTFTISTVQAEDLAVYFCQQDYTSPWTFGGGTELEIK (SEQ ID NO: 20)<br><br>actattgtgatgacccagactcccaaattcctgcttgtatcagcaggagacaggattaccataacctgcaaggccagtcagagtgtgagtaatgatgtagcctggtaccaacagaagccagggcagtctcctaaactgctgatatactatgcatccaatcgctaccctggagtccctgatcgcttcactggcagtggatatgggacggatttcactttcaccatcagcactgtgcaggctgaagacctggcagtttatttctgtcagcaggattatacctctccgtggacgttcggtggaggcaccgagctggaaatcaaa (SEQ ID NO: 26) |
| SAIT-Ang-2-AB-m2E7 | SIVMTQTPKFLLVSAGDRVTITCKASQSVSNDVAWYRQKPGQSPKLLIYYASNRYTGVPDRFTGSGYGTDFTFTISTVQAEDLAVYFCQQDYSSPLTFGARTKLELK (SEQ ID NO: 21)<br><br>agtattgtgatgaccagactcccaaattcctgcttgtgtcagcaggagacagggttaccataacctgcaaggccagtcagagtgtgagtaatgatgtagcttggtaccgacagaagccagggcagtctcctaaactgctgatatactatgcatccaatcgctacactggagtccctgatcgcttcactggcagtggatatgggacggatttcactttcaccatcagcactgtgcaggctgaagacctggcagtttatttctgtcagcaggattatagctctccgctcacgttcggtgctaggaccaagctggagctgaaa (SEQ ID NO: 27) |

(In above Tables 6 and 7, underlined bold letters are CDR1, CDR2, and CDR3 in order)

Example 3

Suppression of Ang-2-Dependent Cell Adhesion

Binding of Ang-2 to other receptors besides Tie2 was verified by testing Ang-2-dependent cell adhesion in a U87MG cell line known to express no Tie2.

Specifically, a 96-well pate was treated with 100 ul of a solution of Ang-2 (R&D systems; 623-AN-025/CF) diluted at a concentration of 10 μg/ml in a phosphate buffered saline (PBS) and incubated at 4° C. for 18 hours to coat the wells with Ang-2. Thereafter, the Ang-2-coated 96 wells were treated with 2% BSA (bovine serum albumin) at 37° C. for 1 hour to block the surfaces not coated with Ang-2.

A brain cancer cell line U87MG (ATCC, HTB-14™) showing about 70 to 80° A) confluency in a T75 flask was trypsinized for detachment, washed twice with a serum-free medium (IMDM (Iscove's Modified Dulbecco's Medium), invitrogen), and re-suspended in 10 ml of IMDM at a concentration of about $3 \times 10^5$ cells/ml. 150 ul of the cell suspension obtained above was added to each well of the 96-well plate prepared in advance which completed coating and blocking processes and incubated in a $CO_2$ incubator at 37° C. for 2 hours to induce cell adhesion.

Then, the wells were washed four times with IMDM warmed to 37° C. to remove unattached cells. The cell adhesion degree was quantified by measuring the amounts of ATP using a CellTiter-Glo reagent (Promega Co.).

Meanwhile, during the cell adhesion, each well was treated with the anti-Ang-2 antibody obtained in Example 2 at a concentration of 50 nM to measure inhibitory degree of Ang-2-dependent cell adhesion. No antibody treatment group was used as a control.

Figure 3:
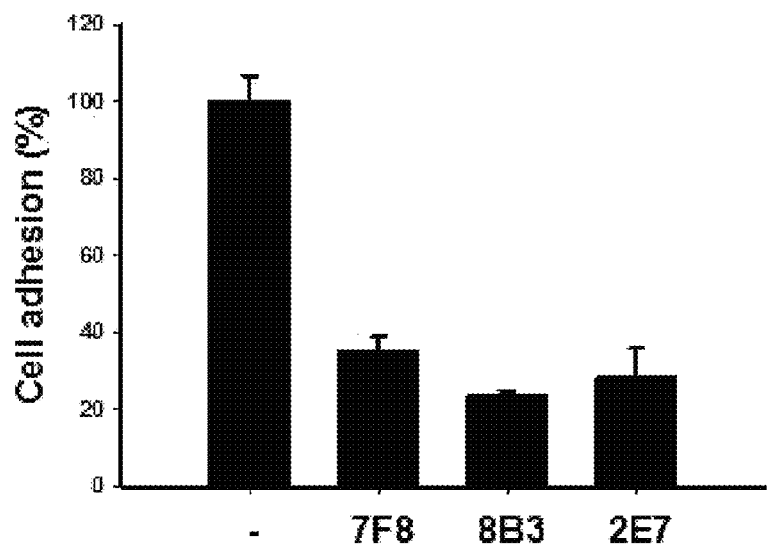
FIG. 3 is a graph showing the degree of inhibition of Ang-2-depedent cell adhesion following the treatment with three anti-Ang-2 antibodies, 7F8, 8B3 and 2E7.

The cell adhesion degrees measured above were compared to the control (adhesion degree 100%) and shown in Table 3 and FIG. 3.

TABLE 8

| Antibody Name | Ang-2-depedent Cell Adhesion Degree (%) |
|---|---|
| Control (no antibody treatment) | 100 |
| SAIT-Ang-2-AB-m7F8 | 35.1 |
| SAIT-Ang-2-AB-m8B3 | 23.6 |
| SAIT-Ang-2-AB-m2E7 | 28.1 |

As confirmed in the above Table 8 and FIG. 3, all of the 3 kinds of anti-Ang-2 antibodies showed Ang-2-dependent cell adhesion inhibitory effects of at least 60%, compared to the control group treated with no antibody.

Further, it was verified whether Tie2 is not actually expressed in the U87MG cell line used in the above. For this, the proteins of U87MG cell line (ATCC, HTB-14™) were developed by sodium dodecyl sulfate-polyacrylamide gel electrophoresis (SDS-PAGE) experiment methods, transferred onto a nitrocellulose paper, and then treated with an antibody to Tie2 (Santa Cruz Biotechnology, SC-324) to conduct western blot methods. A human umbilical vein endothelial cell (HUVEC; ATCC, CRL1730™) line which is well known to express Tie2 was used as a positive control. GAPDH was used as a control regarding the total amount of the proteins loaded to the gels.

The thus obtained results are shown in FIG. 1. As shown in FIG. 1, the U87MG cell line did not express Tie2.

It was verified that Ang-2 is bound to other receptors besides Tie2, by testing Angiopoietin-2 (Ang-2) dependent cell adhesion in the U87MG cell line which was verified not to express Tie2 in the above, Specifically, a 96-well plate was treated with 100 ul of a solution of Ang-2 (R&D systems; 623-AN-025/CF) diluted in a phosphate buffered saline (PBS) at a concentration of 10 μg/ml and incubated at 4° C. for 16 hours to coat the wells with Ang-2. Thereafter, the Ang-2-coated 96 wells were washed twice with PBS and treated with 200 ul of PBS containing 2% (v/v) bovine serum albumin (BSA) at a room temperature for 1 hour for blocking. A well which was only blocked (treated with only BSA) without Ang-2 coating was prepared as a control group.

During the blocking process, a brain cancer cell line U87MG (ATCC, HTB-14™) showing about 70 to 80% confluency in a T75 flask was trypsinized for detachment, washed twice with a serum-free medium (IMDM, invitrogen), and re-suspended in 10 ml of a serum-free medium at a concentration of about $3 \times 10^5$ cells/ml. 150 ul of the cell suspension obtained above was added to each well of the 96-well plate prepared in advance which completed coating and blocking processes and incubated in a $CO_2$ incubator at 37° C. for 2 hours to induce cell adhesion.

Then, the wells were washed four times with the serum-free medium warmed to 37° C. to remove unattached cells. The cell adhesion degree was quantified by measuring luminescence at EnVision® Multilabel Reader (PerkinElmer), 10 min later after 200 ul of a CellTiter-Glo reagent (Promega) diluted in IMDM at 1:1 was added.

Figure 2:
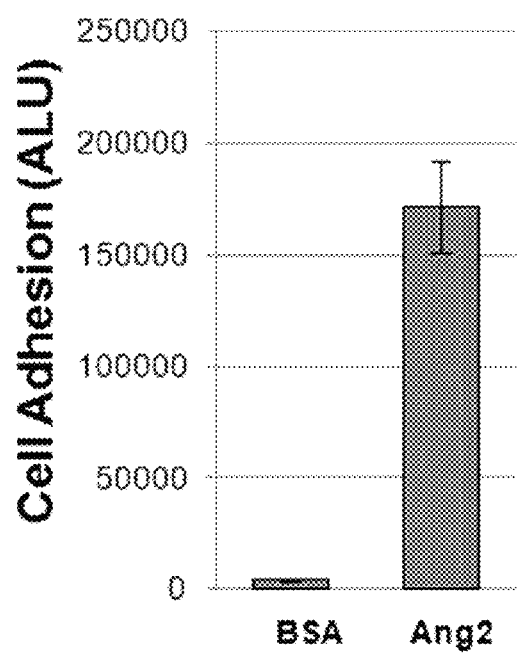
FIG. 2 is a graph showing the level of adhesion of U87MG cells in Ang-2 or BSA coated wells (ALU: arbitrary light unit).

The results are shown in FIG. 2. As shown in FIG. 2, while U87MG cell adhesion hardly occurred in the well treated with only BSA which was prepared as the control group, U87MG cell adhesion occurred at a considerably high level in the well with Ang-2 attached thereto.

Example 4

Influence Test on Ang-2-Tie2 Binding

To see whether the antibodies inhibiting Ang-2-depedent cell adhesion obtained in Example 2 inhibit binding of Ang-2 and Tie2 as well, Ang-2-Tie2 binding competition ELISA was conducted.

Specifically, MaxiSorp™ flat-bottom plate (Nunc) of 96-well was coated with hTie2-Fc (R&D Systems) which is a protein bound with 4 μg/ml of Fc of human IgG1. After that, the plate was washed five times with 0.05% PBST (0.05% (v/v) Tween-20 containing phosphate buffer saline) and then blocked with a 1% (v/v) BSA (bovine serum albumin; Sigma)-containing PBS at a room temperature for 1 hour.

To perform Ang-2:Tie2 competition ELISA, each antibody obtained in Example 2 was placed at various concentrations of 50~0.0000005 nM into each well coated with the hTie2/Fc fusion protein along with 1% (v/v) BSA and 200 ng/ml of a FLAG-tagged hAng-2 and then, the plate was allowed to react at a room temperature for 2 hours and washed five times with PBST. After that, an anti-FLAG antibody (Sigma) conjugated with horseradish peroxidase (HRP) diluted in a BSA-containing PBS at a ratio of 1:5,000 (v/v) was added in an amount of 100 ul to each well to react at a room temperature for 1 hour and then, the plate was washed five times with PBST. Lastly, 100 ul of TMB substrate (Cell Signaling) was added to each well of the plate to induce color development reaction for 3 min. and then, the reaction was ceased by 100 μl of 5N H2SO4 solution and OD450 values were measured on a plate reader (Molecular Devices). The value (Ang-2:Tie2 binding affinity) measured in a control group with no antibody added was set 100%, and the Ang-2:Tie2 binding affinities of test groups with each antibody added were measured as relative values against it.

Figure 4:
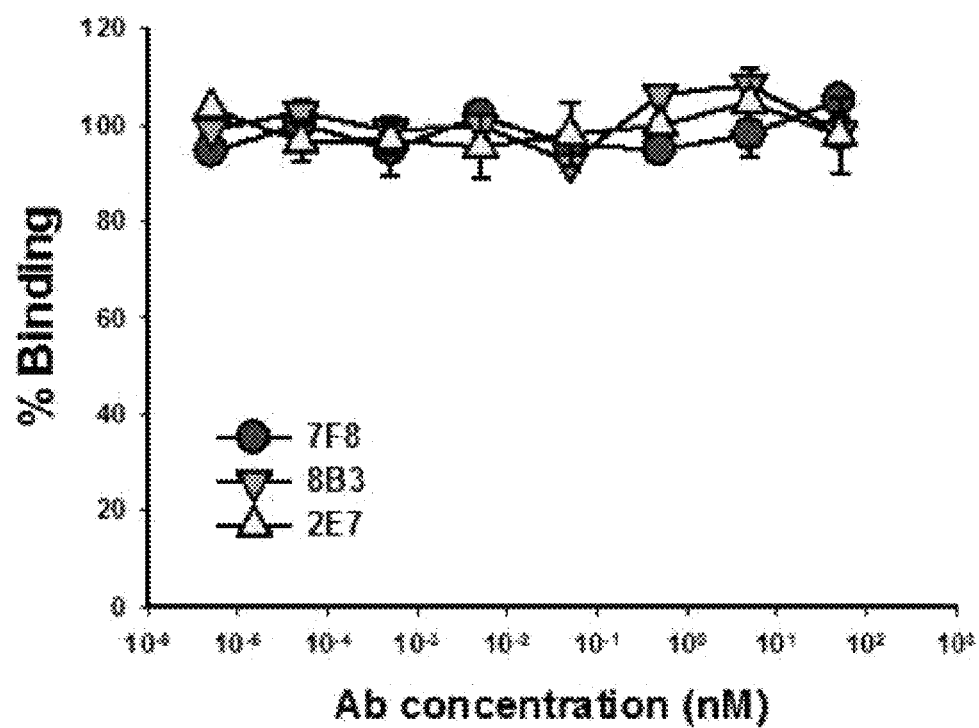
FIG. 4 is a graph showing the binding affinities of Ang-2:Tie2 following treatment with anti-Ang-2 antibodies, measured through color development reaction using HRP.

The obtained results are shown in FIG. 4. As in FIG. 4, the relative Ang-2:Tie2 binding affinities of antibody treatment groups showed no significant differences from the control group with no antibody added. Such results are to verify that the antibodies inhibiting Ang-2-dependent cell adhesion obtained in Example 2 show selective activities which do not neutralize binding affinity between Ang-2 and Tie2.

Example 5

Inhibition of Binding between Ang-2 and Integrin by Anti-Ang-2 Antibody 5.1. Binding Between Ang-2 and Integrin An ELISA plate was coated with diluting solutions of three kinds of integrin (integrin; alpha5beta1 (α5β1; α5: NCBI Accession No. P08648, β1: NCBI Accession No. P05556), alphaVbeta1 (αVβ1; αV: NCBI Accession No. P06756, β1: NCBI Accession No. P05556), and alphaVbeta3 (αVβ3; αV: NCBI Accession No. P06756, β3: NCBI Accession No. P05106); R&D systems) proteins diluted in PBS at a concentration of 5 μg/ml (18 hours, 4° C.) and then blocked with 1% (v/v) BSA at a room temperature for 1 hour. Thereafter, the plate was treated with Ang-2 protein (FLAG-Ang-2, 0.1 ml of Ang-2 protein solution diluted in PBS at a concentration of 10 μg/ml) tagged with a FLAG sequence (DYKDDDDK, Sigma) at N-terminal, incubated at a room temperature for 2 hours, and washed five times with 0.05% PBST (0.05% (v/v) Tween-20-containing phosphate buffer saline). After that, an anti-FLAG antibody (Sigma) conjugated with horseradish peroxidase (HRP) was added to react, and the plate was washed again five times with PBST. Bindings between Ang-2 and the three kinds of integrins were identified indirectly by measuring the amounts of the anti-FLAG antibody remaining in the ELISA plate via color development reaction using TMB (3,3,5,5-tetramethylbenzidine) as a substrate of HRP. As a negative control, those that were blocked only (treated with BSA only) without Ang-2 protein treatment were used.

Figure 5:
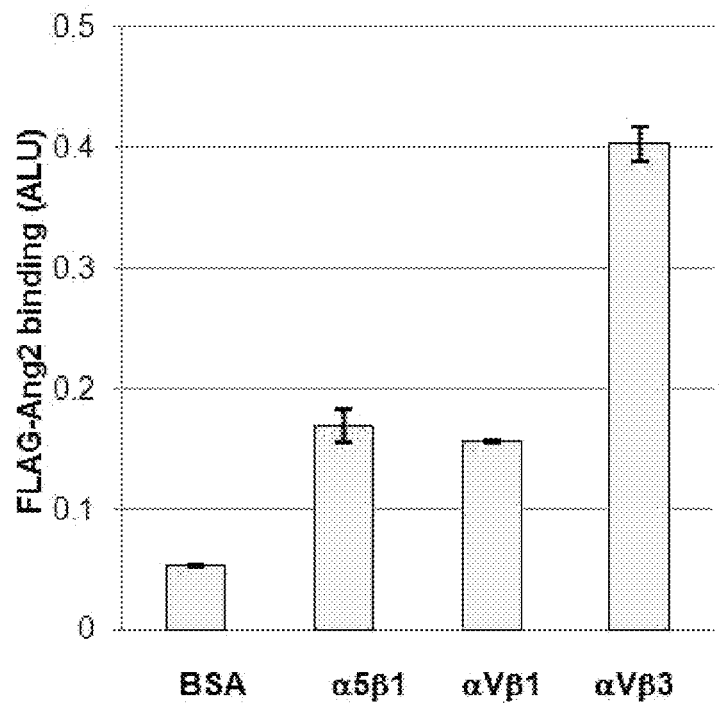
FIG. 5 is a graph showing the extent of binding between Ang-2 protein and various integrin proteins, measured through color development reaction using HRP.

The results are shown in FIG. 5. As shown in FIG. 5, Ang-2 protein was bound to all of the three kinds of integrins.

5.2. Inhibition of Binding Between Ang-2 and Integrin by Anti-Ang-2 Antibody

As it is expected that Ang-2-dependent cell adhesion is involved with several kinds of integrin proteins, the influences of anti-Ang-2 antibody on Ang-2 and integrin protein αVβ3 binding were examined.

An ELISA plate was coated with a diluting solution of a purified alphaVbeta3 protein (αVβ3; αV: NCBI Accession No. P06756, β3: NCBI Accession No. P05106; R&D systems) diluted in PBS at a concentration of 5 μg/ml (18 hours, 4° C.). Then, the anti-Ang-2 antibodies prepared in Example 2 were each added at a concentration of 20 nM along with 10 μg/ml of Ang-2 protein tagged with a FLAG sequence (DYKDDDDK, Sigma) at N-terminal and the plate was incubated at a room temperature for 2 hours. After that, an anti-FLAG antibody (Sigma) conjugated with horseradish peroxidase (HRP) was added to react, and binding between Ang-2 and integrin and inhibitory degree by the antibodies were quantified by measuring the amounts of the anti-FLAG antibody remaining in the ELISA plate via color development reaction using TMB (3,3,5,5-tetramethylbenzidine) as a substrate of HRP. The thus obtained results are shown in FIG. 6.

Figure 6:
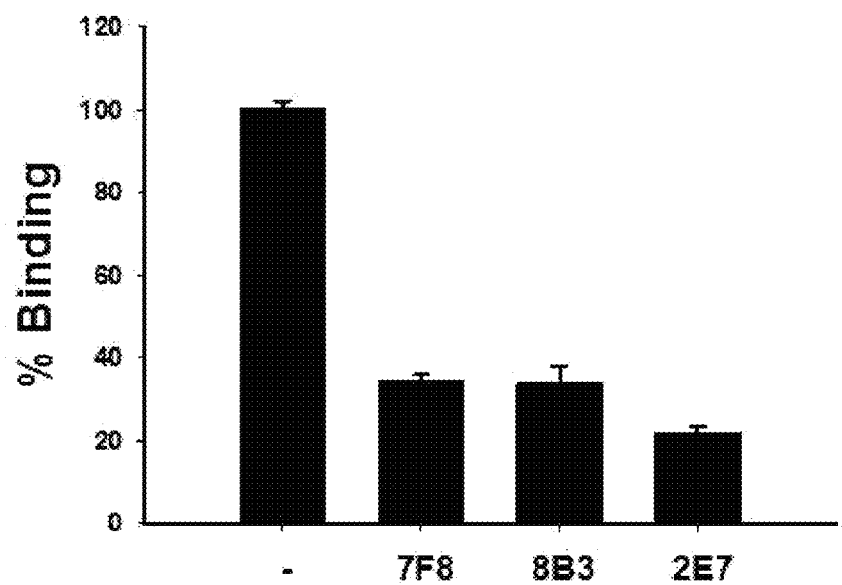
FIG. 6 is a graph showing the level of binding between various Ang-2 antibodies and integrin (alphaVbeta3) quantitatively by an enzyme immunoassay after treatment of anti-Ang-2 antibodies.

As in FIG. 6, the anti-Ang-2 antibodies effectively inhibited binding of Ang-2 and integrin alphaVbeta3 (<50%), compared to the control which did not contain the antibodies.

5.3. Inhibition of Binding Between Ang-2 and Integrin at Cell Membrane

A Chinese Hamster Ovary (CHO) cell line (Korea Research Institute of Bioscience and Biotechnology, Biological Resource Center) was transfected with a pair of cDNA (pTRACER™-CMV2, Invitrogen) encoding green fluorescent protein (GFP) as a transfection marker and cDNA of integrin α5β1 using a lipofectamine 2000 reagent (Invitrogen) according to the manufacturer's recommended experiment methods. Each cDNA (integrin α5, αV, β1, and β3, 4 kinds in total) used for transfection was purchased from Origene and then, corresponding open reading frames thereof were amplified using polymerase chain reaction and cloned into pcDNA3.1(+)/myc-His A (invitrogen).

The transfected cells were incubated under normal cell culture conditions (medium with 10% of Fetal Bovine Serum and Penicillin/streptomycin contained in IMDM, $CO_2$ incubator of 37° C.) for 24 hours.

Thereafter, the cells were detached therefrom and re-suspended at about $2 \times 10^7$ cells/ml in a serum-free medium (IMDM), and 20 μg/ml of FLAG-Ang-2 diluted in 45 ul of this cell solution and 20 μg/ml of each anti-Ang-2 antibody prepared in Example 2 were mixed and then incubated at 4° C. for 1 hour. The cells were fixed with 3% (v/v) formaldehyde, washed with IMDM, and then dyed with anti-FLAG antibody (Sigma) re-conjugated with R-Phycoerythrin, followed by analysis using a flow cytometry.

Figure 7:
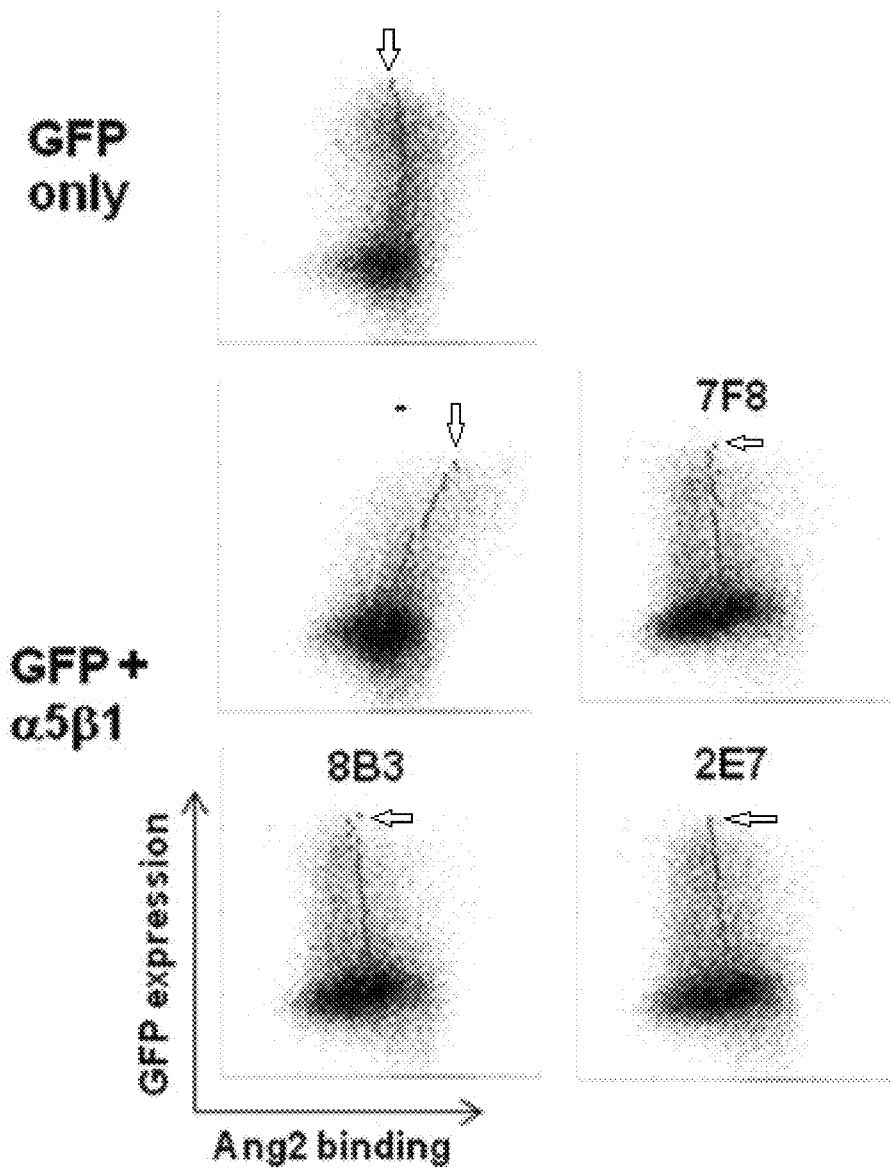
FIG. 7 is cell flow cytometry analysis results showing the level of binding between integrin alpha5beta1 and FLAG-Ang-2 on cell membranes.
Figure 8:
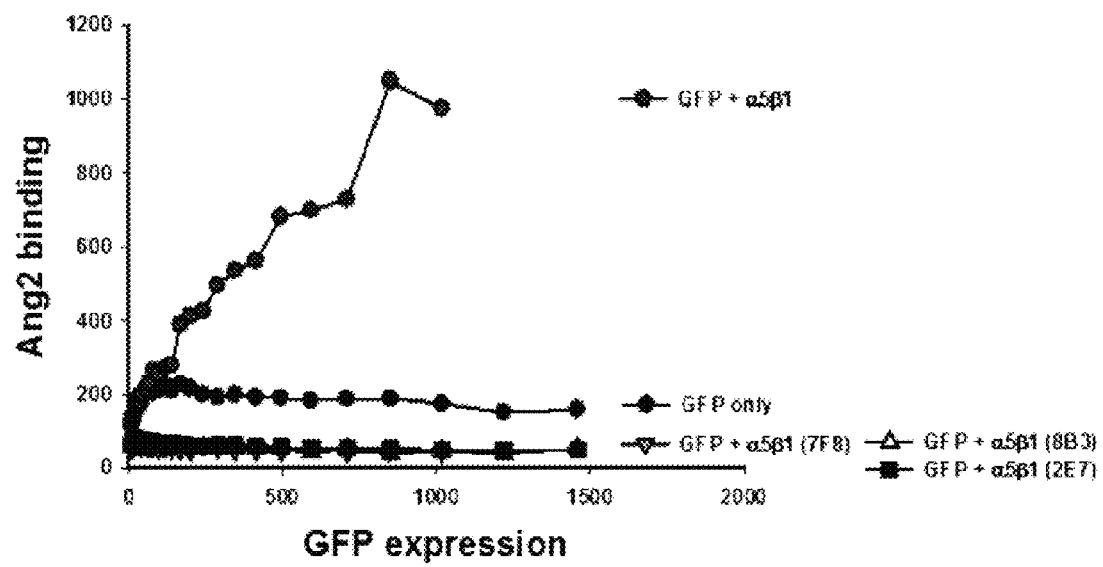
FIG. 8 is a graph of linear-log scale depicting the results of FIG. 7.

The results are shown in FIG. 7 and FIG. 8. In the dot plots of FIG. 7, y-axis indicates the expression of transfection marker GFP, and x-axis indicates Ang-2 binding degree. Dark dots (indicated by arrow) indicate averages of integrin and Ang-2 binding degrees in several cells corresponding to each y-axis section. As the slope of the line formed from upper dark dots in each graph gets low, it indicates high binding degree to Ang-2. In order to clearly demonstrate the Ang-2 binding degrees shown in FIG. 7, the dark dots of FIG. 7 were re-drafted into a graph of linear-log scale, which are shown in FIG. 8. In FIG. 8, it can be seen that Ang-2 was well bound to integrin α5β1 at cell membranes. Meanwhile, it was found that the cells transfected with only integrin-free vectors, which were used as a negative control, bind with integrin irrelevant to the expression of GFP, indicating that Ang-2 was specifically bound to the expressed integrin.

Example 6

Verification of Antigen Recognizing Site (Epitope) of Ang-2 Antibody

To identify each epitope (or specific binding site) of each anti-Ang-2 antibody prepared in Example 2, an ELISA was performed using a recombinant protein where a receptor binding domain (RBD) of Ang-2 protein in the form of being tagged with Flag was mutated by artificial means.

Each well of a 96-well MaxiSorp™ flat-bottom plate (Nunc) was coated with 50 ul (microliter) of 1000 nM antibodies (Example 2). Then, the plate was washed five times with a 0.05% (v/v) Tween-20 containing PBS (PBST) and blocked with a 1% (v/v) BSA containing PBS at a room temperature for 2 hours. 250 ng of each mutant Ang-2 protein obtained by substituting S417, Q418, P419, N421, I434, D448, A449, P452, Y460, N467, K468, or F469 residue of Ang-2 protein tagged with a FLAG sequence (DYKDDDDK, Sigma) at its N-terminal with alanine was added to each well of the plate, which was then allowed to react at a room temperature for 2 hours.

The plate was washed five times with a 0.05% (v/v) Tween-20 containing PBS, reacted with an anti-FLAG antibody (SIGMA) conjugated with HRP which was diluted in a 1% (v/v) BSA containing PBS at a ratio of 1:5,000 (v/v) at a room temperature for 1 hour, and washed five times with a 0.1% (v/v) Tween-20 containing PBS.

Finally, 50 ul of TMB substrates (Cell signaling) was added to each well of the plate to induce color development reaction at a room temperature for 3 min. and the reaction was ceased by the addition of 50 ul of Stop solution (Cell signaling) and then, OD450 values were measured on a plate reader (Molecular Devices). By comparing binding affinities with mutated Ang-2 to those of unmutated Ang-2, each epitope of Ang-2 antibodies was identified. The thus obtained measurement results of the binding affinities (%) of mutant Ang-2 against the binding affinity of the native Ang-2 are shown in the following Table 9.

TABLE 9

| | % at RBD binding | | | | | | | | | | | |
|---|---|---|---|---|---|---|---|---|---|---|---|---|
| | Loop1 | | | | | Loop2 | | | Loop3 | | | Loop4 |
| | 417 | 418 | 419 | 421 | 434 | 448 | 449 | 452 | 460 | 467 | 468 | 469 |
| 7F8 | 93.95 | 52.80 | 87.98 | 94.21 | 100.05 | 98.27 | 94.10 | 94.10 | 95.73 | 89.82 | 99.70 | 99.61 |
| 8B3 | 95.36 | 4.10 | 8.70 | 102.36 | 99.37 | 96.06 | 88.51 | 102.15 | 100.40 | 95.14 | 104.78 | 105.75 |
| 2(E)7 | 98.29 | 0.60 | 88.63 | 98.94 | 101.54 | 96.92 | 90.89 | 90.07 | 98.70 | 95.98 | 100.87 | 101.56 |

Figure 9:
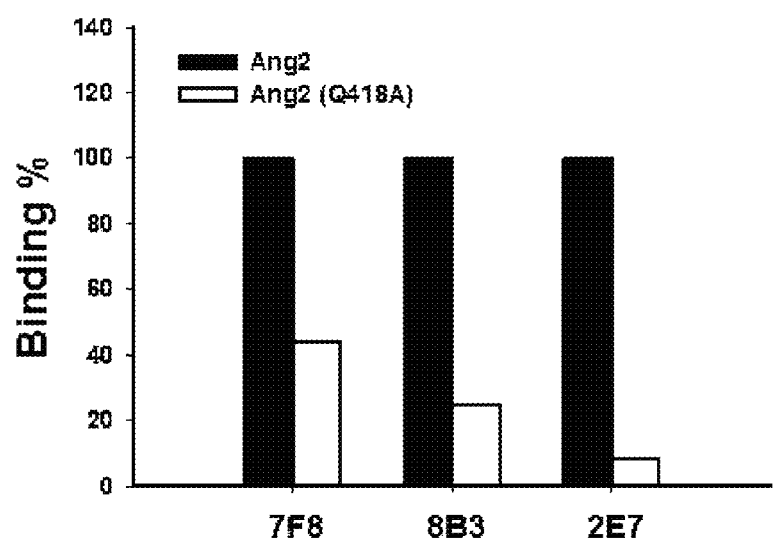
FIG. 9 is a graph showing the binding affinities between several anti-Ang-2 antibodies and Ang-2 proteins, each of which was measured using a wild-type Ang-2 protein and an Ang-2 protein having Q418A mutation.

An ELISA experiment was performed using Q418A mutant protein which shows the most distinct decline in binding affinities by mutation in Table 9, and the results are shown in FIG. 9.

It can be seen from FIG. 9 that the Ang-2 protein binding affinities of the anti-Ang-2 antibodies were remarkably declined by Q418A mutation of Ang-2 protein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. An anti-ANG-2 antibody or an antigen-binding fragment thereof comprising,
a heavy chain variable region comprising
CDR-H1 comprising the amino acid sequence of SEQ ID NO: 1,
CDR-H2 comprising the amino acid sequence of SEQ ID NO: 14, having the sequence Y-I-$X_1$-Y-$X_2$-G-$X_3$-T-$X_4$-Y-N-P-S-L-K-S, wherein $X_1$ is serine (S) or asparagine (N), $X_2$ is serine (S) or arginine (R), $X_3$ is serine (S) or asparagine (N), and $X_4$ is serine (S) or aspartic acid (D),
and CDR-H3 comprising an amino acid sequence selected from the group consisting of SEQ ID NOS: 4-6; and
a light chain variable region comprising CDR-L1 comprising the amino acid sequence of SEQ ID NOS: 7 or 8,
CDR-L2 comprising the amino acid sequence of SEQ ID NOS: 9 or 10, and
CDR-L3 comprising the amino acid sequence of SEQ ID NO: 15, having the sequence Q-Q-D-Y-$X_5$-S-P-$X_6$-T, wherein $X_5$ is serine (S), or threonine (T), and $X_6$ is proline (P), leucine (L), or tryptophan (W).

2. The anti-ANG-2 antibody or the antigen-binding fragment thereof according to claim 1, wherein the anti-ANG-2 antibody or the antigen-binding fragment thereof comprises
heavy chain complementarity determining regions consisting of a polypeptide (CDR-H1) comprising the amino acid sequence of SEQ ID NO: 1, a polypeptide (CDR-H2) comprising the amino acid sequence of SEQ ID NOS: 2 or 3, and a polypeptide (CDR-H3) comprising an amino acid sequence selected from the group consisting of SEQ ID NOS: 4-6; and
light chain complementarity determining regions consisting of a polypeptide (CDR-L1) comprising the amino acid sequence of SEQ ID NOS: 7 or 8, a polypeptide (CDR-L2) comprising the amino acid sequence of SEQ ID NOS: 9 or 10, and a polypeptide (CDR-L3) comprising an amino acid sequence selected from the group consisting of SEQ ID NOS: 11-13.

3. The anti-ANG-2 antibody or the antigen-binding fragment thereof according to claim 2, wherein the anti-ANG-2 antibody or the antigen-binding fragment thereof comprises:
a heavy chain variable region comprising an amino acid sequence selected from the group consisting of SEQ ID NOS: 16-18, and
a light chain variable region comprising an amino acid sequence selected from the group consisting of SEQ ID NOS: 19-21.

4. The anti-ANG-2 antibody or the antigen-binding fragment thereof according to claim 1, wherein the anti-ANG-2 antibody or antibody fragment is a monoclonal antibody or antibody fragment.

5. The anti-ANG-2 antibody or the antigen-binding fragment thereof according to claim 4, wherein the anti-ANG-2 antibody or antigen-binding fragment thereof is obtained from the hybridoma of accession number KCLRF-BP-00292, KCLRF-BP-00293, or KCLRF-BP-00294.

6. The anti-ANG-2 antibody or the antigen-binding fragment thereof according to claim 1, wherein the anti-ANG-2 antibody or antigen-binding fragment thereof is a mouse antibody or antigen-binding fragment, a mouse-human chimeric antibody or antigen-binding fragment, a humanized antibody or antigen-binding fragment, a human antibody, or any antigen-binding fragment.

7. The anti-ANG-2 antibody or the antigen-binding fragment thereof according to claim 1, wherein the antigen-binding fragment is selected from the group consisting of a scFv, a (scFv)2, a Fab, a Fab' and a F(ab')2 of the anti-ANG-2 antibody.

8. A hybridoma cell line of accession number KCLRF-BP-00292, KCLRF-BP-00293, or KCLRF-BP-00294, which produces an anti-ANG-2 antibody.

9. A pharmaceutical composition comprising the anti-ANG-2 antibody or the antigen-binding fragment thereof of claim 1 and a pharmaceutically acceptable carrier.

10. An anti-ANG-2 antibody, or an antigen-binding portion thereof, comprising:
(a) a heavy chain variable domain comprising a CDR-H1 having an amino acid sequence of SEQ ID NO. 1, a CDR-H2 having an amino acid sequence of SEQ ID NO: 2, and a CDR-H3 having an amino acid sequence of SEQ ID NO. 4; and a light chain variable domain comprising a CDR-L1 having an amino acid sequence of SEQ ID NO: 7, a CDR-L2 having an amino acid sequence of SEQ ID NO. 9, and a CDR-L3 having an amino acid sequence of SEQ ID NO. 11;
(b) a heavy chain variable domain comprising a CDR-H1 having an amino acid sequence of SEQ ID NO. 1, a CDR-H2 having an amino acid sequence of SEQ ID NO. 3, and a CDR-H3 region having an amino acid sequence of SEQ ID NO. 5; and a light chain variable domain comprising a CDR-L1 having an amino acid sequence of SEQ ID NO. 8, a CDR-L2 having an amino acid sequence of SEQ ID NO. 10, and a CDR-L3 having an amino acid sequence of SEQ ID NO. 12; or
(c) a heavy chain variable domain comprising a CDR-H1 having an amino acid sequence of SEQ ID NO. 1, a CDR-H2 having an amino acid sequence of SEQ ID NO. 2, and a CDR-H3 having an amino acid sequence of SEQ ID NO. 6; and a light chain variable domain comprising a CDR-L1 having an amino acid sequence of SEQ ID NO. 8, a CDR-L2 having an amino acid sequence of SEQ ID NO. 9, and a CDR-L3 having an amino acid sequence of SEQ ID NO. 13.

* * * * *

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 1

Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 2

Tyr Ile Ser Tyr Ser Gly Ser Thr Ser Tyr Asn Pro Ser Leu Lys Ser
1               5                   10                  15
```

```
<210> SEQ ID NO 3
<211> LENGTH: 16
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 3

Tyr Ile Asn Tyr Arg Gly Asn Thr Asp Tyr Asn Pro Ser Leu Lys Ser
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 4

Ser Thr Phe Gly His Tyr Val Ser Ser Met Asp Tyr
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 5

Gly Asn Phe Glu Gly Ala Met Asp Tyr
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 6

Gly Asp Tyr Gly Asn Tyr Val Gly Pro Met Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 7

Lys Ala Ser Gln Ser Ala Ser Asn Asp Val Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 8

Lys Ala Ser Gln Ser Val Ser Asn Asp Val Ala
1               5                   10

<210> SEQ ID NO 9
```

```
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 9

Tyr Ala Ser Asn Arg Tyr Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 10

Tyr Ala Ser Asn Arg Tyr Pro
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 11

Gln Gln Asp Tyr Ser Ser Pro Pro Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 12

Gln Gln Asp Tyr Thr Ser Pro Trp Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 13

Gln Gln Asp Tyr Ser Ser Pro Leu Thr
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic (CDR-H2 of anti-Ang2 antibody)
<220> FEATURE:
<221> NAME/KEY: MOD_RES
<222> LOCATION: (3)..(3)
<223> OTHER INFORMATION: Xaa is Ser(S) or Asn(N)
<220> FEATURE:
<221> NAME/KEY: MOD_RES
<222> LOCATION: (5)..(5)
<223> OTHER INFORMATION: Xaa is Ser(S) or Arg(R)
<220> FEATURE:
```

```
<221> NAME/KEY: MOD_RES
<222> LOCATION: (7)..(7)
<223> OTHER INFORMATION: Xaa is Ser(S) or Asn(N)
<220> FEATURE:
<221> NAME/KEY: MOD_RES
<222> LOCATION: (9)..(9)
<223> OTHER INFORMATION: Xaa is Ser(S) or Asp(D)

<400> SEQUENCE: 14

Tyr Ile Xaa Tyr Xaa Gly Xaa Thr Xaa Tyr Asn Pro Ser Leu Lys Ser
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)
<220> FEATURE:
<221> NAME/KEY: MOD_RES
<222> LOCATION: (5)..(5)
<223> OTHER INFORMATION: Xaa is Ser(S) or Thr(T)
<220> FEATURE:
<221> NAME/KEY: MOD_RES
<222> LOCATION: (8)..(8)
<223> OTHER INFORMATION: Xaa is Pro(P), Leu(L), or Trp(W)

<400> SEQUENCE: 15

Gln Gln Asp Tyr Xaa Ser Pro Xaa Thr
1               5

<210> SEQ ID NO 16
<211> LENGTH: 112
<212> TYPE: PRT
<213> ORGANISM: Artificial Sequence
<220> FEATURE:
<223> OTHER INFORMATION: Synthetic (Heavy chain variable region of
      anti-Ang2 antibody)

<400> SEQUENCE: 16

Val Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Thr Ser Asp Tyr
            20                  25                  30

Ala Trp Asn Trp Ile Arg Gln Phe Pro Gly Asn Lys Leu Glu Trp Met
        35                  40                  45

Gly Tyr Ile Ser Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Pro Glu Asp Thr Ala Thr Tyr Tyr Cys Ala
                85                  90                  95

Arg Ser Thr Phe Gly His Tyr Val Ser Ser Met Asp Tyr Trp Gly Gln
            100                 105                 110

<210> SEQ ID NO 17
<211> LENGTH: 109
<212> TYPE: PRT
<213> ORGANISM: Artificial Sequence
<220> FEATURE:
<223> OTHER INFORMATION: Synthetic (Heavy chain variable region of
      anti-Ang2 antibody)

<400> SEQUENCE: 17

Val Gln Leu Gln Glu Ser Gly Pro Gly Leu Val Lys Pro Ser Gln Ser
1               5                   10                  15
```

Leu Ser Leu Ser Cys Thr Val Thr Gly Tyr Ser Ile Ala Ser Asp Tyr
            20                  25                  30

Ala Trp Asn Trp Ile Arg Gln Phe Pro Gly Asn Lys Val Glu Trp Met
        35                  40                  45

Gly Tyr Ile Asn Tyr Arg Gly Asn Thr Asp Tyr Asn Pro Ser Leu Lys
    50                  55                  60

Ser Arg Ser Ser Ile Asn Arg Asp Thr Ser Lys Asn Gln Phe Phe Leu
65                  70                  75                  80

Gln Leu Asn Ser Val Thr Thr Gly Asp Thr Ala Thr Tyr Tyr Cys Ala
                85                  90                  95

Arg Gly Asn Phe Glu Gly Ala Met Asp Tyr Trp Gly Gln
            100                 105

<210> SEQ ID NO 18
<211> LENGTH: 112
<212> TYPE: PRT
<213> ORGANISM: Artificial Sequence
<220> FEATURE:
<223> OTHER INFORMATION: Synthetic (Heavy chain variable region of
      anti-Ang2 antibody)

<400> SEQUENCE: 18

Leu Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Thr Ser Asp Tyr
            20                  25                  30

Ala Trp Asn Trp Ile Arg Gln Phe Pro Gly Asn Lys Leu Glu Trp Met
        35                  40                  45

Gly Tyr Ile Ser Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Leu Thr Thr Glu Asp Thr Ala Thr Tyr Tyr Cys Ala
                85                  90                  95

Arg Gly Asp Tyr Gly Asn Tyr Val Gly Pro Met Asp Tyr Trp Gly Gln
            100                 105                 110

<210> SEQ ID NO 19
<211> LENGTH: 107
<212> TYPE: PRT
<213> ORGANISM: Artificial Sequence
<220> FEATURE:
<223> OTHER INFORMATION: Synthetic (Light chain variable region of
      anti-Ang2 antibody)

<400> SEQUENCE: 19

Ser Ile Val Met Thr Gln Thr Pro Lys Leu Leu Leu Val Ser Ala Gly
1               5                   10                  15

Asp Arg Val Thr Ile Thr Cys Lys Ala Ser Gln Ser Ala Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Ala Ile Ser Thr Val Gln Ala
65                  70                  75                  80

Glu Asp Leu Ala Ile Tyr Phe Cys Gln Gln Asp Tyr Ser Ser Pro Pro
                85                  90                  95

```
Thr Phe Gly Gly Gly Thr Lys Leu Glu Ile Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Synthetic (Light chain variable region of
      anti-Ang2 antibody)

<400> SEQUENCE: 20

```
Thr Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Pro Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Glu Leu Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic (Light chain variable region of
      anti-Ang2 antibody)

<400> SEQUENCE: 21

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Arg Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Arg Thr Lys Leu Glu Leu Lys
            100                 105
```

<210> SEQ ID NO 22
<211> LENGTH: 363
<212> TYPE: DNA
<213> ORGANISM: Artificial Sequence
<220> FEATURE:
<223> OTHER INFORMATION: Synthetic (Nucleotide sequence encoding heavy
      chain variable region of anti-Ang2 antibody of SEQ ID NO: 16)

<400> SEQUENCE: 22

```
gatgtgcagc ttcaggagtc gggacctggc ctggtgaaac cttctcagtc tctgtccctc    60
acctgcactg tcactggcta ctcaatcacc agtgattatg cctggaactg gatccggcag   120
tttccaggaa acaaactgga gtggatgggt tacataagct acagtggtag cactagctac   180
aacccatctc tcaaaagtcg aatctctatc actcgagaca catccaagaa tcagttcttc   240
ctgcagctga attctgtgac acctgaggac acagccacat attactgtgc aagatcaact   300
tttggtcact acgtcagttc tatggactac tggggtcaag aacctcagt caccgtctcc   360 tca                                                                 363
```

<210> SEQ ID NO 23
<211> LENGTH: 354
<212> TYPE: DNA
<213> ORGANISM: Artificial Sequence
<220> FEATURE:
<223> OTHER INFORMATION: Synthetic (Nucleotide sequence encoding heavy
      chain variable region of anti-Ang2 antibody of SEQ ID NO: 17)

<400> SEQUENCE: 23

```
gatgtgcagc ttcaggagtc gggacctggc ctggtgaaac cttctcagtc tctgtccctc    60
tcctgcactg tcactggcta ctcaatcgcc agtgattatg cctggaactg gatccggcag   120
tttccaggaa acaaagtgga gtggatgggc tacataaact accgtggaaa cactgactac   180
aacccatctc tcaaaagtcg aagctctatc aatcgagaca catccaagaa ccagttcttc   240
ctgcaattga attctgtgac tactggggac acagccacat attactgtgc aagaggtaac   300
ttcgaaggag ctatggacta ctggggtcaa ggaacctcag tcaccgtctc ctca         354
```

<210> SEQ ID NO 24
<211> LENGTH: 363
<212> TYPE: DNA
<213> ORGANISM: Artificial Sequence
<220> FEATURE:
<223> OTHER INFORMATION: Synthetic (Nucleotide sequence encoding heavy
      chain variable region of anti-Ang2 antibody of SEQ ID NO: 18)

<400> SEQUENCE: 24

```
gatgtgcagc ttcaggagtc gggacctggc ctggtgaaac cttctcagtc tctgtccctc    60
acctgcactg tcactggcta ctcaatcacc agtgattatg cctggaactg gatccggcag   120
tttccaggaa acaaactgga gtggatgggc tacataagct acagtggtag tactagctac   180
aacccatctc tcaaaagtcg aatctctatc actcgagaca catccaagaa ccagttcttc   240
ctacagttga attctttgac tactgaggac acagccacat attactgtgc aagaggggac   300
tatggtaact acgtgggacc tatggactac tggggtcaag aacctcagt caccgtctcc   360 tca                                                                 363
```

<210> SEQ ID NO 25
<211> LENGTH: 321
<212> TYPE: DNA
<213> ORGANISM: Artificial Sequence
<220> FEATURE:
<223> OTHER INFORMATION: Synthetic (Nucleotide sequence encoding Light
      chain variable region of anti-Ang2 antibody of SEQ ID NO: 19)

<400> SEQUENCE: 25

```
agtattgtga tgacccagac tcccaaactc ctgcttgttt cagcaggaga cagggttacc    60
ataacctgca aggccagtca gagtgcgagc aatgatgttg cttggtacca acagaagcca   120
gggcagtctc ctaaactgct gatatactat gcatccaatc gctacactgg agtccctgat   180
```

```
cgcttcactg gcagtggata tgggacggat tcactttcg ccatcagcac tgtgcaggct      240
gaagacctgg caatttattt ctgtcagcag gattatagct ctccaccgac gttcggtgga      300
ggcaccaagc tggaaatcaa a                                                321
```

```
<210> SEQ ID NO 26
<211> LENGTH: 321
<212> TYPE: DNA
<213> ORGANISM: Artificial Sequence
<220> FEATURE:
<223> OTHER INFORMATION: Synthetic (Nucleotide sequence encoding Light
      chain variable region of anti-Ang2 antibody of SEQ ID NO: 20)

<400> SEQUENCE: 26
```

```
actattgtga tgacccagac tcccaaattc ctgcttgtat cagcaggaga caggattacc      60
ataacctgca aggccagtca gagtgtgagt aatgatgtag cctggtacca acagaagcca      120
gggcagtctc ctaaactgct gatatactat gcatccaatc gctaccctgg agtccctgat      180
cgcttcactg gcagtggata tgggacggat tcactttcg ccatcagcac tgtgcaggct      240
gaagacctgg cagtttattt ctgtcagcag gattatacct ctccgtggac gttcggtgga      300
ggcaccgagc tggaaatcaa a                                                321
```

```
<210> SEQ ID NO 27
<211> LENGTH: 321
<212> TYPE: DNA
<213> ORGANISM: Artificial Sequence
<220> FEATURE:
<223> OTHER INFORMATION: Synthetic (Nucleotide sequence encoding Light
      chain variable region of anti-Ang2 antibody of SEQ ID NO: 21)

<400> SEQUENCE: 27
```

```
agtattgtga tgacccagac tcccaaattc ctgcttgtgt cagcaggaga cagggttacc      60
ataacctgca aggccagtca gagtgtgagt aatgatgtag cttggtaccg acagaagcca      120
gggcagtctc ctaaactgct gatatactat gcatccaatc gctacactgg agtccctgat      180
cgcttcactg gcagtggata tgggacggat tcactttcg ccatcagcac tgtgcaggct      240
gaagacctgg cagtttattt ctgtcagcag gattatagct ctccgctcac gttcggtgct      300
aggaccaagc tggagctgaa a                                                321
```

```
<210> SEQ ID NO 28
<211> LENGTH: 496
<212> TYPE: PRT
<213> ORGANISM: Artificial Sequence
<220> FEATURE:
<223> OTHER INFORMATION: Synthetic (Human Ang2)

<400> SEQUENCE: 28
```

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95
```

-continued

```
Leu Glu Asn Tyr Ile Gln Asp Asn Met Lys Lys Glu Met Val Glu Ile
                100                 105                 110
Gln Gln Asn Ala Val Gln Asn Thr Ala Val Met Ile Glu Ile Gly
            115                 120                 125
Thr Asn Leu Leu Asn Gln Thr Ala Glu Gln Thr Arg Lys Leu Thr Asp
        130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
        210                 215                 220
Ser Ile Ile Glu Glu Leu Gly Lys Lys Ile Val Thr Ala Thr Val Asn
225                 230                 235                 240
Asn Ser Val Leu Gln Lys Gln Gln His Asp Leu Met Glu Thr Val Asn
                245                 250                 255
Asn Leu Leu Thr Met Met Ser Thr Ser Asn Ser Ala Lys Asp Pro Thr
            260                 265                 270
Val Ala Lys Glu Glu Gln Ile Ser Phe Arg Asp Cys Ala Glu Val Phe
        275                 280                 285
Lys Ser Gly His Thr Thr Asn Gly Ile Tyr Thr Leu Thr Phe Pro Asn
        290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
            340                 345                 350
Tyr Trp Leu Gly Asn Glu Phe Val Ser Gln Leu Thr Asn Gln Gln Arg
        355                 360                 365
Tyr Val Leu Lys Ile His Leu Lys Asp Trp Glu Gly Asn Glu Ala Tyr
        370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
            420                 425                 430
Cys Ile Cys Lys Cys Ser Gln Met Leu Thr Gly Gly Trp Trp Phe Asp
        435                 440                 445
Ala Cys Gly Pro Ser Asn Leu Asn Gly Met Tyr Tyr Pro Gln Arg Gln
        450                 455                 460
Asn Thr Asn Lys Phe Asn Gly Ile Lys Trp Tyr Tyr Trp Lys Gly Ser
465                 470                 475                 480
Gly Tyr Ser Leu Lys Ala Thr Thr Met Met Ile Arg Pro Ala Asp Phe
                485                 490                 495
```